US009567402B2

(12) United States Patent
Liu

(10) Patent No.: US 9,567,402 B2
(45) Date of Patent: Feb. 14, 2017

(54) INTERNALIZING HUMAN MONOCLONAL ANTIBODIES TARGETING PROSTATE AND OTHER CANCER CELLS

(71) Applicant: The Regents of the University of California, Oakland, CA (US)

(72) Inventor: Bin Liu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/205,101

(22) Filed: Mar. 11, 2014

(65) Prior Publication Data
US 2014/0271685 A1    Sep. 18, 2014

Related U.S. Application Data

(60) Provisional application No. 61/785,118, filed on Mar. 14, 2013.

(51) Int. Cl.
| | |
|---|---|
| *C07K 16/28* | (2006.01) |
| *A61K 47/48* | (2006.01) |
| *G01N 33/574* | (2006.01) |
| *C07K 16/30* | (2006.01) |
| *A61K 51/10* | (2006.01) |

(52) U.S. Cl.
CPC ..... *C07K 16/2896* (2013.01); *A61K 47/48384* (2013.01); *A61K 47/48415* (2013.01); *A61K 47/48484* (2013.01); *A61K 47/48638* (2013.01); *A61K 51/1072* (2013.01); *A61K 51/1093* (2013.01); *C07K 16/3069* (2013.01); *G01N 33/57434* (2013.01); *G01N 33/57492* (2013.01); *C07K 2317/21* (2013.01); *C07K 2317/34* (2013.01); *C07K 2317/565* (2013.01); *C07K 2317/567* (2013.01); *C07K 2317/622* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 6,469,779 B2 | 10/2002 | Baer et al. | |
| 6,818,749 B1 | 11/2004 | Kashmiri et al. | |
| 8,865,873 B2 | 10/2014 | Liu et al. | |
| 2003/0108966 A1* | 6/2003 | Mather | C07K 16/2896 435/7.23 |
| 2005/0186214 A1 | 8/2005 | Liu et al. | |
| 2010/0233165 A1 | 9/2010 | Liu et al. | |
| 2015/0071937 A1 | 3/2015 | Liu et al. | |

FOREIGN PATENT DOCUMENTS

| | | |
|---|---|---|
| WO | WO 2005/062977 | 7/2005 |
| WO | WO 2009/039192 | 3/2009 |

OTHER PUBLICATIONS

Mariuzza et al. (Annu. Rev. Biophys. Biophys. Chem. 1987; 16: 139-159).*
US Office Action dated Dec. 14, 2012 issued in U.S. Appl. No. 12/724,282.
US Final Office Action dated Jul. 19, 2013 issued in U.S. Appl. No. 12/724,282.
US Notice of Allowance dated Jun. 12, 2014 issued in U.S. Appl. No. 12/724,282.
US Office Action dated Sep. 3, 2015 issued in U.S. Appl. No. 14/486,943.
US Final Office Action dated Apr. 19, 2016 issued in U.S. Appl. No. 14/486,943.
PCT International Search Report and Written Opinion dated May 4, 2009 issued in PCT/US2008/076704 (WO 2009/039192).
PCT International Preliminary Report on Patentability dated Mar. 24, 2010 issued in PCT/US2008/076704 (WO 2009/039192).
Canadian Office Action dated Oct. 30, 2014 issued in CA 2,699,394.
Canadian Examination Report dated Oct. 16, 2015 issued in CA 2,699,394.
EP Supplementary Search Report dated Aug. 31, 2010 issued in EP08831767.2.
EP Partial Search Report dated Jul. 4, 2011 issued in EP011159671.4.
EP Extended Search Report dated Sep. 22, 2011 issued in EP011159671.4.
EP Office Action dated Apr. 5, 2013 issued in EP011159671.4.
Becerril et al. (1999) "Toward Selection of Internalizing Antibodies from Phage Libraries," *Biochem. Biophys. Res. Commun.*, 255(2):386-393.
Birklé et al. (2003) "Role of tumor-associated gangliosides in cancer progression," *Biochimie*, (Paris) 85(3-4):455-463.
Bonner et al. (1997) "Laser Capture Microdissection: Molecular Analysis of Tissue," *Science*, 278(5342):1481-1483.
Cai et al. (1995) "Anti-melanoma antibodies from melanoma patients immunized with genetically modified autologous tumor cells: Selection of specific antibodies from single-chain Fv fusion phage libraries," *Proc. Natl. Acad. Sci. U.S.A.*, 92: 6537-6541.
Clynes et al. (2000) "Inhibitory Fc receptors modulate in vivo cytotoxicity against tumor targets," *Nat. Med.*, 6(4):443-446.
Covell et al. (2005) "Linking tumor cell cytotoxicity to mechanism of drug action: An integrated analysis of gene expression, small-molecule screening and structural databases," *Proteins*, 59:403-433.
Dall'Acqua et al. (2005) "Antibody humanization by framework shuffling," *Methods*, 36:43-60.
de Kruif et al. (1995) "Rapid selection of cell subpopulation-specific human monoclonal antibodies from a synthetic phage antibody library," *Proc. Natl. Acad. Sci. U.S.A.*, 92:3938-3942.
Degen et al. (1998) "MEMD, a new cell adhesion molecule in metastasizing human melanoma cell lines, is identical to ALCAM (activated leukocyte cell adhesion molecule)," *Am. J. Pathol.*, 152(3):805-813.

(Continued)

*Primary Examiner* — Brad Duffy
*Assistant Examiner* — Nelson B Moseley, II
(74) *Attorney, Agent, or Firm* — Tom Hunter; Weaver Austin Villeneuve & Sampson LLP

(57) ABSTRACT

In various embodiments various cancer specific antibodies and immunoconjugates are provided. In certain embodiments the antibodies specifically bind and are internalized into a prostate cancer cell, where the antibodies specifically (Continued)

binds cells that express or overexpress a CD46, and where the antibodies specifically bind sushi domain 1 of said CD46 (CD46 CPP1).

30 Claims, 9 Drawing Sheets

(56) References Cited

OTHER PUBLICATIONS

Emmert-Buck et al. (1996) "Laser Capture Microdissection," *Science*, 274:998-1001.
"Epitope" Definition, *Stedman's Online Medical Dictionary*, 27th Edition, Oct. 5, 2010, Wolters Kluwer Health, Inc.; available at www.stedmans.com, 1 page.
Fuh et al. (2006) "Structure-function studies of two synthetic anti-vascular endothelial growth factor Fabs and comparison with the Avastin™ Fab," *J. Biol. Chem.*, 281(10):6625-6631.
Gao et al. (2003) "De novo identification of tumor-specific internalizing human antibody-receptor pairs by phage-display methods," *Journal of Immunological Methods*, 274:185-197.
Garraway et al. (2006) "From Integrated Genomics to Tumor Lineage Dependency," *Cancer Res.*, 66:2506-2508.
Geuijen et al. (2005) "A proteomic approach to tumour target identification using phage display, affinity purification and mass spectrometry," *Eur. J. Cancer*, 41:178-187.
Greenspan et al. (1999) "Defining epitopes: It's not as easy as it seems," *Nature Biotechnology*, 7: 936-37.
Hakomori (2001) "Tumor-associated carbohydrate antigens defining tumor malignancy: basis for development of anti-cancer vaccines," *Adv. Exp. Med. Biol.*, 491:369-402.
Hanisch (2001) "O-Glycosylation of the mucin type," *Biol. Chem.*, 382:143-149.
Hughes et al. (2001) "Counting the Uncountable: Statistical Approaches to Estimating Microbial Diversity," *Appl. Environ. Microbiol.*, 67(10):4399-4406.
Hughes et al. (2005) "The Application of Rarefaction Techniques to Molecular Inventories of Microbial Diversity," *Meth. Enzymol.*, 397:292-308.
Huie et al. (2001) "Antibodies to human fetal erythroid cells from a nonimmune phage antibody library," *Proc. Natl. Acad. Sci., U.S.A.*, 98:2682-2687.
Kobata et al. (2005) "Altered glycosylation of proteins produced by malignant cells, and application for the diagnosis and immunotherapy of tumours," *Immunol. Cell Biol.*, 83:429-439.
Kristiansen et al. (2005) "Expression profiling of microdissected matched prostate cancer samples reveals CD166/MEMD and CD24 as new prognostic markers for patient survival," *J. Pathol.*, 205:359-376.
Lekkerkerker et al. (1999) "Phage antibodies against human dendritic cell subpopulations obtained by flow cytometry-based selection on freshly isolated cells," *J. Immunol. Methods*, 231:53-63.
Liu et al. (2000) "Applying Phage Antibodies to Proteomics: Selecting Single Chain Fv Antibodies to Antigens Blotted on Nitrocellulose," *Anal. Biochem.*, 286:119-128.
Liu et al. (2002) "Towards proteome-wide production of monoclonal antibody by phage display," *J. Mol. Biol.*, 315:1063-1073.
Liu et al. (2004) "Mapping Tumor Epitope Space by Direct Selection of Single-Chain Fv Antibody Libraries on Prostate Cancer Cells," *Cancer Research*, 64(2):704-710.
Lu et al. (2004) "Application of laser capture microdissection to phage display peptide library screening," *Oral Surg. Oral Med. Oral Pathol. Oral Radiol. Endod.*, 98(6):692-697.
Liu et al., (Jun. 2007) "Recombinant full-length human IgG1s targeting hormone-refractory prostate cancer," *J. Mol. Med.*, 85:1113-1123.
MacCallum et al. (1996) "Antibody-antigen Interactions: Contact Analysis and Binding Site Topography," *J. Mol. Biol.*, 262:732-745.
Marks et al. (1991) "By-passing immunization: Human antibodies from V-gene libraries displayed on phage," *J. Mol. Biol.*, 222:581-597.
Marks et al. (1992) "By-passing immunization: building high affinity human antibodies by chain shuffling," *Biotechnology*, (N.Y.) 10:779-783.
Marks et al. (1992) "Molecular evolution of proteins on filamentous phage. Mimicking the strategy of the immune system," *J. Biol. Chem.*, 267(23):16007-16010.
McWhirter et al. (2006) "Antibodies selected from combinatorial libraries block a tumor antigen that plays a key role in immunomodulation," *Proc. Natl. Acad. Sci. USA.*, 103(4):1041-1046.
Molecular & Cellular Proteomics: Editorial Policies and Practices, Apr. 2006, 12 pages.
Nielsen et al. (2002) "Therapeutic efficacy of anti-ErbB2 immunoliposomes targeted by a phage antibody selected for cellular endocytosis," *Biochim. Biophys. Acta*, 1591:109-118.
O'Connell et al. (2002) "Phage versus Phagemid Libraries for Generation of Human Monoclonal antibodies," *J. Mol. Biol.*, 321:49-56.
Paul (1993) "Structure and Function of Immunoglobulins," *Fundamental Immunology*, 3rd Edition, Chapter 9, pp. 292-295.
Piazza et al. (2005) "Internalization and recycling of ALCAM/CD166 detected by a fully human single-chain recombinant antibody," *J. Cell Sci.*, 118(7):1515-1525.
Pini et al. (1998) "Design and use of a phage display library. Human antibodies with subnanomolar affinity against a marker of angiogenesis eluted from a two-dimensional gel," *J. Biol. Chem.*, 273(34):21769-21776.
Pirollo et al. (2006) "Tumor-Targeting Nanoimmunoliposome Complex for Short Interfering RNA Delivery," *Hum. Gene Ther.*, 17:117-124.
Poul et al. (2000) "Selection of tumor-specific internalizing human antibodies from phage libraries," *J. Mol. Biol.*, 301:1149-1161.
Ruan et al. (2006) "Identification of Clinically Significant Tumor Antigens by Selecting Phage Antibody Library on Tumor Cells in Situ Using Laser Capture Microdissection," *Molecular & Cellular Proteomics*, 5(12):2364-2373.
Saifullah et al. (2004) "Expression and Characterization of a Novel CD6 Ligand in Cells Derived from Joint and Epithelial Tissues," *J. Immunol.*, 173:6125-6133.
Saito et al. (2004) "Distribution of Liposomes into Brain and Rat Brain Tumor Models by Convection-Enhanced Delivery Monitored with Magnetic Resonance Imaging," *Cancer Res.*, 64:2572-2579.
Saito et al. (2005) "Gadolinium-loaded liposomes allow for real-time magnetic resonance imaging of convection-enhanced delivery in the primate brain," *Exp. Neurol.*, 196:381-389.
Sharon et al. (2005) "Recombinant Polyclonal Antibodies for Cancer Therapy," *J. Cell. Biochem.*, 96:305-313.
Silacci et al. (2005) "Design, construction, and characterization of a large synthetic human antibody phage display library," *Proteomics*, 5:2340-2350.
Simone et al. (1998) "Laser-capture microdissection: opening the microscopic frontier to molecular analysis," *Trends Genet.*, 14(7):272-276.
Song et al. (2005) "Antibody mediated in vivo delivery of small interfering RNAs via cell-surface receptors," *Nat. Biotechnol.*, 23(6):709-717.
Ugorski et al. (2002) "Sialyl Lewis$^a$: a tumor-associated carbohydrate antigen involved in adhesion and metastatic potential of cancer cells," *Acta Biochim. Pol.*, 49(2):303-311.
Yao et al. (2005) "Targeting Pancreatic Islets with Phage Display Assisted by Laser Pressure Catapult Microdissection," *Am. J. Pathol.*, 166(2):625-636.

\* cited by examiner

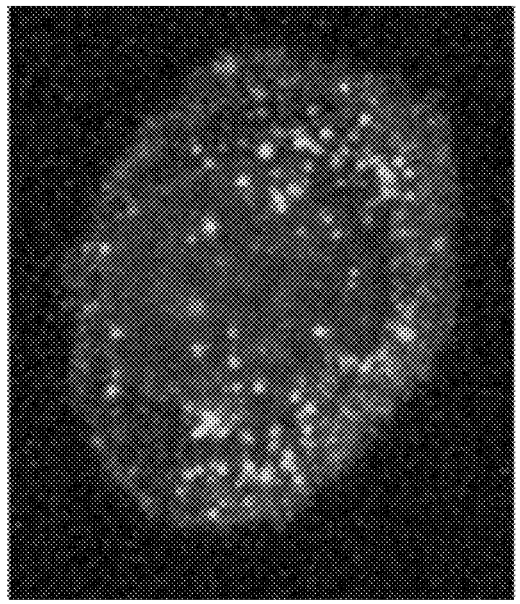
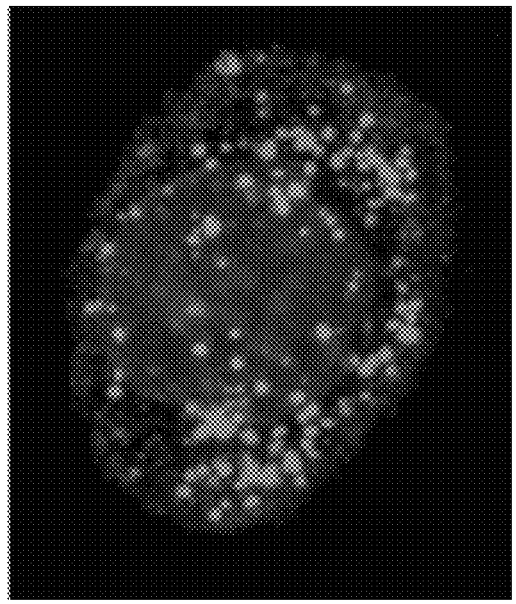
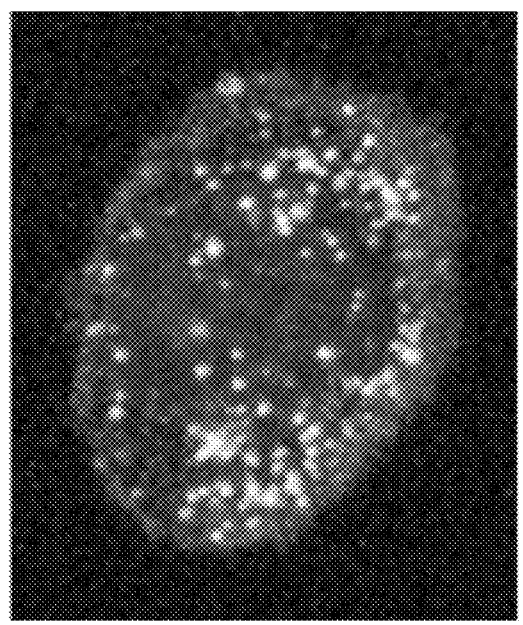
Fig. 4

Heavy chain variable region:

```
2B10VH    QVQLQEPGGGLVQPGRSLRLSCAASGFTFDDYAMHWVRQAPGKGLEWVGRIKSKTDEGTT
UA20VH    QVQLQESGGGLVKPGGSLRLSCAASGFTFSMAMMWVRQAPGKGLEWVGRIKSKTDEGTT
          *****:*****:**.******** ****  : *: *************************

2B10VH    DYAAPVKGRFSISRDDSKNTLYLQMNSLKTEDTGVYYCTATKGLGGSKLGQGTLVTVSS
UA20VH    DYAAPVKGRFSISRDDSKNTLYLQMNSLKTEDTGVYYCTATKGLGGSKLGQGTLVTVSS
          ************************************************************
```

Light chain variable region:

```
2B10VL    QSVLTQPPSASGTPGQRVTISCSGSSSNIGSNTVSWSRQLPGTAPKLLIYSNDQRPSGVP
UA20VL    QSVLTQPPSASGTPGQRVTISCSGSSSNIGNNTVNWSRQLPGTAPKLLIYSNDQRPSGVP
          ****************************** ** *.***********************

2B10VL    DRFSGSKSGTSASLAITGLQPEDEADYYCGTWDSSLSAYVFGTGTKLTVL
UA20VL    DRFSGSKSGTSASLAITGLQPEDEADYYCGTWDSSLSAYVFGTGTKLTVL
          **************************************************
```

Fig. 8

```
SEQUENCE LISTING

<160> NUMBER OF SEQ ID NOS: 42

<210> SEQ ID NO 1
<211> LENGTH: 32
<212> TYPE: PRT
<213> ORGANISM: Homo sapiens

<400> SEQUENCE: 1

Lys Pro Tyr Tyr Glu Ile Gly Glu Arg Val Asp Tyr Lys Cys Lys Lys
1               5                   10                  15

Gly Tyr Phe Tyr Ile Pro Pro Leu Ala Thr His Thr Ile Cys Asp Arg
            20                  25                  30

<210> SEQ ID NO 2
<211> LENGTH: 15
<212> TYPE: PRT
<213> ORGANISM: Artificial
<220> FEATURE:
<223> OTHER INFORMATION: Peptide linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 10
<212> TYPE: PRT
<213> ORGANISM: Artificial
<220> FEATURE:
<223> OTHER INFORMATION: Peptide linker

<400> SEQUENCE: 3

Gly Gly Gly Gly Ser Gly Gly Gly Gly Ser
1               5                   10

<210> SEQ ID NO 4
<211> LENGTH: 5
<212> TYPE: PRT
<213> ORGANISM: Artificial
<220> FEATURE:
<223> OTHER INFORMATION: Peptide linker

<400> SEQUENCE: 4

Gly Gly Gly Gly Ser
1               5

<210> SEQ ID NO 5
<211> LENGTH: 20
<212> TYPE: PRT
<213> ORGANISM: Artificial
<220> FEATURE:
<223> OTHER INFORMATION: Peptide linker

<400> SEQUENCE: 5

Gly Ser Gly Gly Gly Gly Ser Gly Gly Gly Gly Ser Gly Gly Ser Gly
1               5                   10                  15

Gly Gly Gly Ser
            20
```

```
<210> SEQ ID NO 6
<211> LENGTH: 6
<212> TYPE: PRT
<213> ORGANISM: Artificial
<220> FEATURE:
<223> OTHER INFORMATION: Peptide linker

<400> SEQUENCE: 6

Ser Gly Gly Gly Gly Ser
1               5

<210> SEQ ID NO 7
<211> LENGTH: 4
<212> TYPE: PRT
<213> ORGANISM: Artificial
<220> FEATURE:
<223> OTHER INFORMATION: Peptide linker

<400> SEQUENCE: 7

Gly Gly Gly Ser
1

<210> SEQ ID NO 8
<211> LENGTH: 4
<212> TYPE: PRT
<213> ORGANISM: Artificial
<220> FEATURE:
<223> OTHER INFORMATION: Peptide linker

<400> SEQUENCE: 8

Val Pro Gly Val
1

<210> SEQ ID NO 9
<211> LENGTH: 5
<212> TYPE: PRT
<213> ORGANISM: Artificial
<220> FEATURE:
<223> OTHER INFORMATION: Peptide linker

<400> SEQUENCE: 9

Val Pro Gly Val Gly
1               5

<210> SEQ ID NO 10
<211> LENGTH: 6
<212> TYPE: PRT
<213> ORGANISM: Artificial
<220> FEATURE:
<223> OTHER INFORMATION: Peptide linker

<400> SEQUENCE: 10

Gly Val Pro Gly Val Gly
1               5

<210> SEQ ID NO 11
<211> LENGTH: 8
<212> TYPE: PRT
<213> ORGANISM: Artificial
<220> FEATURE:
<223> OTHER INFORMATION: Peptide linker

<400> SEQUENCE: 11

Gly Val Gly Val Pro Gly Val Gly
1               5
```

```
<210> SEQ ID NO 12
<211> LENGTH: 10
<212> TYPE: PRT
<213> ORGANISM: Artificial
<220> FEATURE:
<223> OTHER INFORMATION: Peptide linker

<400> SEQUENCE: 12

Val Pro Gly Val Gly Val Pro Gly Val Gly
1               5                   10

<210> SEQ ID NO 13
<211> LENGTH: 7
<212> TYPE: PRT
<213> ORGANISM: Artificial
<220> FEATURE:
<223> OTHER INFORMATION: Peptide linker

<400> SEQUENCE: 13

Gly Gly Ser Ser Arg Ser Ser
1               5

<210> SEQ ID NO 14
<211> LENGTH: 18
<212> TYPE: PRT
<213> ORGANISM: Artificial
<220> FEATURE:
<223> OTHER INFORMATION: Peptide linker

<400> SEQUENCE: 14

Gly Gly Ser Ser Arg Ser Ser Ser Gly Gly Gly Ser Gly Gly
1               5                   10                  15

Gly Gly

<210> SEQ ID NO 15
<211> LENGTH: 119
<212> TYPE: PRT
<213> ORGANISM: Artificial
<220> FEATURE:
<223> OTHER INFORMATION: Single chain antibody

<400> SEQUENCE: 15

Gln Val Gln Leu Gln Glu Pro Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Gly Arg Ile Lys Ser Lys Thr Asp Glu Gly Thr Thr Asp Tyr Ala Ala
        50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Gly Val Tyr
                85                  90                  95

Tyr Cys Thr Ala Thr Lys Gly Leu Gly Gly Ser Lys Leu Gly Gln Gly
            100                 105                 110

Thr Leu Val Thr Val Ser Ser
        115

<210> SEQ ID NO 16
<211> LENGTH: 119
<212> TYPE: PRT
```

```
<213> ORGANISM: Artificial
<220> FEATURE:
<223> OTHER INFORMATION: Single chain antibody

<400> SEQUENCE: 16

Gln Val Gln Leu Gln Glu Pro Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Gly Arg Ile Lys Ser Lys Thr Asp Glu Gly Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Gly Val Tyr
                85                  90                  95

Tyr Cys Thr Ala Thr Lys Gly Leu Gly Gly Ser Lys Leu Gly Gln Gly
            100                 105                 110

Thr Leu Val Thr Val Ser Ser
        115

<210> SEQ ID NO 17
<211> LENGTH: 110
<212> TYPE: PRT
<213> ORGANISM: Artificial
<220> FEATURE:
<223> OTHER INFORMATION: Single chain antibody

<400> SEQUENCE: 17

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Ser Trp Ser Arg Gln Leu Pro Gly Thr Ala Pro Lys Leu Leu
            35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Pro Glu Asp Glu Ala Asp Tyr Tyr Cys Gly Thr Trp Asp Ser Ser Leu
                85                  90                  95

Ser Ala Tyr Val Phe Gly Thr Gly Thr Lys Leu Thr Val Leu
            100                 105                 110

<210> SEQ ID NO 18
<211> LENGTH: 110
<212> TYPE: PRT
<213> ORGANISM: Artificial
<220> FEATURE:
<223> OTHER INFORMATION: Single chain antibody

<400> SEQUENCE: 18

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Thr Val Asn Trp Ser Arg Gln Leu Pro Gly Thr Ala Pro Lys Leu Leu
            35                  40                  45
```

```
Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
 65                 70                  75                  80

Pro Glu Asp Glu Ala Asp Tyr Tyr Cys Gly Thr Trp Asp Ser Ser Leu
                85                  90                  95

Ser Ala Tyr Val Phe Gly Thr Gly Thr Lys Leu Thr Val Leu
            100                 105                 110
```

<210> SEQ ID NO 19
<211> LENGTH: 62
<212> TYPE: PRT
<213> ORGANISM: Homo sapiens

<400> SEQUENCE: 19

```
Cys Glu Glu Pro Pro Thr Phe Glu Ala Met Glu Leu Ile Gly Lys Pro
 1               5                  10                  15

Lys Pro Tyr Tyr Glu Ile Gly Glu Arg Val Asp Tyr Lys Cys Lys Lys
                20                  25                  30

Gly Tyr Phe Tyr Ile Pro Pro Leu Ala Thr His Thr Ile Cys Asp Arg
            35                  40                  45

Asn His Thr Trp Leu Pro Val Ser Asp Asp Ala Cys Tyr Arg
 50                  55                  60
```

<210> SEQ ID NO 20
<211> LENGTH: 242
<212> TYPE: PRT
<213> ORGANISM: Artificial
<220> FEATURE:
<223> OTHER INFORMATION: Single chain antibody

<400> SEQUENCE: 20

```
Gln Val Gln Leu Gln Glu Ser Gly Gly Gly Leu Val Lys Pro Gly Gly
 1               5                  10                  15

Pro Leu Arg Leu Ser Cys Ala Ala Ser Gly Phe Thr Phe Ser Ser Tyr
                20                  25                  30

Gly Met Tyr Trp Val Arg Gln Ala Pro Gly Lys Gly Leu Glu Trp Val
            35                  40                  45

Ser Thr Leu Ser Arg Ser Gly Ser Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Ile Ala Val Ala Gly Asn Tyr Phe Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ser Tyr Val Leu Thr Gln Asp Pro Ala Val
130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Glu Arg Pro Gly Gln Ala
                165                 170                 175

Pro Leu Leu Val Ile Tyr Gly Lys Asn Asn Arg Pro Ser Gly Ile Pro
            180                 185                 190
```

```
Asp Arg Phe Ser Gly Ser Asn Ser Gly Ser Thr Ala Thr Leu Thr Ile
            195                 200                 205

Ser Arg Val Glu Ala Gly Asp Glu Gly Asp Tyr Tyr Cys Gln Val Trp
210                 215                 220

Asp Ser Ile Asn Glu Gln Val Val Phe Gly Gly Gly Thr Lys Val Thr
225                 230                 235                 240

Val Leu

<210> SEQ ID NO 21
<211> LENGTH: 241
<212> TYPE: PRT
<213> ORGANISM: Artificial
<220> FEATURE:
<223> OTHER INFORMATION: Single chain antibody

<400> SEQUENCE: 21

Gln Val Gln Leu Val Gln Ser Gly Gly Gly Val Val Gln Pro Gly Arg
1               5                   10                  15

Ser Leu Arg Leu Ser Cys Ala Ala Thr Gly Ile Pro Phe Ser Gly Ser
            20                  25                  30

Gly Met His Trp Val Arg Gln Ala Pro Gly Lys Gly Leu Glu Trp Val
        35                  40                  45

Thr Met Ile Trp Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Arg Asp Lys Gly Val Arg Ser Met Asp Val Trp Gly Leu Gly Thr
            100                 105                 110

Thr Val Thr Val Ser Ser Gly Gly Gly Gly Ser Gly Gly Gly Gly Ser
        115                 120                 125

Gly Gly Gly Gly Ser Asn Phe Met Leu Thr Gln Pro Pro Ser Val Ser
    130                 135                 140

Val Ala Pro Gly Gln Thr Ala Lys Ile Thr Cys Asp Gly Tyr Ser Ile
145                 150                 155                 160

Arg Thr Lys Ser Val His Trp Tyr Gln Gln Lys Pro Gly Gln Ala Pro
                165                 170                 175

Val Val Val Val His Asp Ser Asp Arg Pro Ser Gly Ile Pro Glu
            180                 185                 190

Arg Phe Ser Gly Ser Asn Ser Gly Thr Thr Ala Thr Leu Thr Ile Ser
        195                 200                 205

Arg Val Glu Ala Gly Asp Glu Ala Asp Tyr Tyr Cys Gln Ala Trp Asp
    210                 215                 220

Ser Ile Ser Glu Glu Val Val Phe Gly Gly Gly Thr Lys Leu Thr Val
225                 230                 235                 240

Leu

<210> SEQ ID NO 22
<211> LENGTH: 240
<212> TYPE: PRT
<213> ORGANISM: Artificial
<220> FEATURE:
<223> OTHER INFORMATION: Single chain antibody

<400> SEQUENCE: 22

Gln Val Gln Leu Gln Glu Ser Gly Gly Gly Leu Val Gln Pro Gly Gly
```

```
              1               5                  10                 15
            Ser Leu Arg Leu Ser Cys Ser Ala Ser Gly Phe Thr Phe Gly Thr Tyr
                            20                  25                 30

Ala Met Arg Trp Val Arg Gln Thr Ser Gly Lys Gly Leu Glu Trp Val
                            35                  40                 45

Ser Gly Ile Gly Val Ser Gly Asp Ala Tyr Tyr Thr Asp Ser Val Arg
                50                          55                 60

Gly Arg Phe Thr Ile Ser Arg Asp Asn Ser Lys Asn Thr Leu Tyr Leu
            65                  70                  75                     80

Gln Met Asn Thr Leu Arg Ala Glu Asp Thr Ala Thr Tyr Tyr Cys Thr
                            85                  90                 95

Arg Lys Ser Ser Thr Thr Ser Asn Asp Tyr Trp Gly Arg Gly Thr Leu
                            100                 105                110

Val Thr Val Ser Gly Gly Gly Gly Ser Gly Gly Gly Ser Gly
                            115                 120                125

Gly Gly Gly Ser Ser Tyr Val Leu Thr Gln Asp Pro Ala Val Ser Val
                130                         135                140

Ala Leu Gly Gln Thr Val Arg Ile Thr Cys Gln Gly Asp Asn Ile Gly
            145                 150                 155                    160

Ser Lys Ser Val His Trp Tyr Gln Gln Lys Pro Gly Gln Ala Pro Val
                            165                 170                175

Leu Val Val Tyr Asp Asp Ser Asp Arg Pro Ser Gly Ile Pro Glu Arg
                            180                 185                190

Phe Ser Gly Ser Asn Ser Gly Thr Thr Ala Thr Leu Thr Ile Ser Ser
                            195                 200                205

Val Glu Ala Gly Asp Glu Ala Asp Tyr Tyr Cys Gln Ala Trp Asp Ser
                            210                 215                220

Ile Ser Glu His Val Ile Phe Gly Gly Gly Thr Lys Val Thr Val Leu
            225                 230                 235                    240

<210> SEQ ID NO 23
<211> LENGTH: 241
<212> TYPE: PRT
<213> ORGANISM: Artificial
<220> FEATURE:
<223> OTHER INFORMATION: Single chain antibody

<400> SEQUENCE: 23

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Ser Ser Gly Trp Tyr Tyr Phe Asp Tyr Trp Gly Gln Gly
                100                 105                 110

Thr Leu Val Thr Val Ser Ser Gly Gly Gly Gly Ser Gly Gly Gly Gly
                115                 120                 125

Ser Gly Gly Gly Gly Ser Asp Ile Gln Met Thr Gln Ser Pro Ser Phe
```

```
                   130                 135                 140
Leu Ser Ala Ser Val Gly Asp Arg Ile Thr Ile Thr Cys Arg Ala Ser
145                 150                 155                 160

His Asp Ile Ser Ser Tyr Phe Ala Trp Tyr Gln Gln Lys Pro Gly Lys
                165                 170                 175

Ala Pro Lys Pro Leu Ile Tyr Ala Ala Ser Thr Leu Gln Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

Leu Gly Ser Tyr Pro Leu Thr Phe Gly Gly Gly Thr Lys Leu Glu Ile
225                 230                 235                 240

Lys

<210> SEQ ID NO 24
<211> LENGTH: 245
<212> TYPE: PRT
<213> ORGANISM: Artificial
<220> FEATURE:
<223> OTHER INFORMATION: Single chain antibody

<400> SEQUENCE: 24

Gln Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Asp Tyr Gly Asp Tyr Ala Gly Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser His Val Ile Leu Thr Gln Asp Pro
    130                 135                 140

Ala Val Ser Val Ala Leu Gly Gln Thr Val Arg Ile Thr Cys Gln Gly
145                 150                 155                 160

Asp Ser Leu Lys Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Thr Thr Ala Ser Leu
        195                 200                 205

Thr Ile Thr Gly Ala Gln Ala Glu Asp Glu Ala Asp Tyr Tyr Cys His
    210                 215                 220

Ser Arg Asp Ser Ser Gly Thr His Leu Arg Val Phe Gly Gly Gly Thr
225                 230                 235                 240

Lys Leu Thr Val Leu
                245
```

```
<210> SEQ ID NO 25
<211> LENGTH: 244
<212> TYPE: PRT
<213> ORGANISM: Artificial
<220> FEATURE:
<223> OTHER INFORMATION: Single chain antibody

<400> SEQUENCE: 25

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Glu Gly Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Gly Val Tyr
                85                  90                  95

Tyr Cys Thr Ala Thr Lys Gly Leu Gly Gly Ser Lys Leu Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Pro Glu Asp Glu Ala Asp Tyr Tyr Cys Gly
    210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 26
<211> LENGTH: 245
<212> TYPE: PRT
<213> ORGANISM: Artificial
<220> FEATURE:
<223> OTHER INFORMATION: Single chain antibody

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Arg Ala Pro Gly Lys Gly Leu Glu Trp Val
        35                  40                  45

Ala Val Ile Ser Tyr Asp Gly Ser Asn Gln Tyr Tyr Ala Asp Ser Val
    50                  55                  60
```

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Ser Arg Pro Gly Gly Tyr Ala Ser Gly Ser Thr Val Ala Tyr
            100                 105                 110

Trp Gly Gln Gly Thr Pro Val Thr Val Ser Gly Gly Gly Ser
            115                 120                 125

Gly Gly Gly Gly Ser Gly Gly Gly Ser Ser Glu Leu Thr Gln
        130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Leu Leu Val Ile Tyr Gly Gln Asn Ile Arg Pro
            180                 185                 190

Ser Gly Ile Pro Asp Arg Phe Ser Gly Ser Ser Ser Gly Asn Ser Ala
            195                 200                 205

Ser Leu Thr Ile Thr Gly Ala Gln Ala Glu Asp Glu Ala Asp Tyr Tyr
    210                 215                 220

Cys His Ser Arg Asp Ser Ser Gly Lys Tyr Val Phe Gly Val Gly Thr
225                 230                 235                 240

Lys Val Thr Val Leu
                245

<210> SEQ ID NO 27
<211> LENGTH: 237
<212> TYPE: PRT
<213> ORGANISM: Artificial
<220> FEATURE:
<223> OTHER INFORMATION: Single chain antibody

<400> SEQUENCE: 27

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Gly Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
            195                 200                 205

Ala Glu Asp Glu Ala Asp Tyr Tyr Cys Asn Ser Arg Asp Ser Ser Gly
210                 215                 220

Asn Pro Val Phe Gly Gly Gly Thr Lys Val Thr Val Leu
225                 230                 235

<210> SEQ ID NO 28
<211> LENGTH: 237
<212> TYPE: PRT
<213> ORGANISM: Artificial
<220> FEATURE:
<223> OTHER INFORMATION: Single chain antibody

<400> SEQUENCE: 28

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
210                 215                 220

Asn Pro Val Phe Gly Gly Gly Thr Lys Val Thr Val Leu
225                 230                 235

<210> SEQ ID NO 29
<211> LENGTH: 243
<212> TYPE: PRT
<213> ORGANISM: Artificial
<220> FEATURE:
<223> OTHER INFORMATION: Single chain antibody

<400> SEQUENCE: 29

Gln Val Gln Leu Gln Glu Ser Gly Gly Gly Leu Val Gln Leu Gly Gly

```
  1               5                  10                 15
Ser Leu Arg Leu Ser Cys Ala Ala Ser Gly Phe Thr Phe Ser Ser Tyr
             20                  25                 30

Ala Met Ser Trp Val Arg Gln Ala Pro Gly Lys Gly Leu Glu Trp Val
             35                  40                 45

Ser Ala Ile Ser Gly Ser Gly Gly Ser Thr Tyr Tyr Ala Asp Ser Val
             50                  55                 60

Lys Gly Arg Phe Thr Ile Ser Arg Asp Asn Ser Lys Asn Thr Leu Tyr
 65                  70                  75                 80

Leu Gln Met Ser Ser Leu Arg Ala Glu Asp Thr Ala Phe Tyr Tyr Cys
                 85                  90                 95

Ala Asn Ser Ala Tyr Thr Gly Gly Trp Tyr Asp Tyr Trp Gly His Gly
            100                 105                110

Thr Leu Val Thr Val Ser Ser Gly Gly Gly Gly Ser Gly Gly Gly Gly
            115                 120                125

Ser Gly Gly Gly Gly Ser Ser Glu Leu Thr Gln Asp Pro Ala Val
130                 135                 140

Ser Val Ala Leu Gly Gln Thr Val Lys Ile Thr Cys Gln Gly Asp Ser
145                 150                 155                160

Leu Arg Thr Tyr Tyr Ala Ser Trp Tyr Gln Gln Arg Pro Gly Gln Ala
                165                 170                175

Pro Val Leu Val Ile Tyr Gly Glu Asn Ser Arg Pro Ser Gly Ile Pro
            180                 185                190

Asp Arg Phe Ser Gly Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
210                 215                 220

Asp Ser Ser Gly Asn His Leu Arg Val Phe Gly Gly Thr Lys Leu
225                 230                 235                 240

Thr Val Leu
```

<210> SEQ ID NO 30
<211> LENGTH: 238
<212> TYPE: PRT
<213> ORGANISM: Artificial
<220> FEATURE:
<223> OTHER INFORMATION: Single chain antibody

<400> SEQUENCE: 30

```
Gln Val Asn Leu Arg Glu Ser Gly Gly Gly Leu Val Gln Pro Gly Gly
 1               5                  10                 15

Phe Leu Arg Leu Ser Cys Ala Ala Phe Gly Thr Phe Ser Gly Tyr
             20                  25                 30

Trp Met Ser Trp Val His Pro Ala Pro Gly Lys Gly Leu Glu Trp Val
             35                  40                 45

Ala Asn Ile Lys Gln Asp Gly Ser Glu Lys Phe Tyr Val Asp Ser Val
             50                  55                 60

Lys Gly Arg Phe Thr Ile Ser Arg Asp Asn Ala Lys Asn Ser Leu Phe
 65                  70                  75                 80

Leu Gln Met Asn Ser Leu Arg Ala Glu Asp Thr Ala Val Tyr Phe Cys
                 85                  90                 95

Ala Arg Gly Leu Leu Ser Asp Tyr Trp Gly Gln Gly Thr Leu Val Pro
            100                 105                110

Val Ser Ser Gly Gly Gly Gly Ser Gly Gly Gly Gly Ser Gly Gly Gly
            115                 120                125
```

```
Gly Ser Asn Phe Met Leu Thr Gln Pro Pro Ser Val Ser Val Ala Pro
        130                 135                 140

Gly Lys Thr Ala Ser Leu Thr Cys Gly Gly Tyr Asn Ile Gly Thr Lys
145                 150                 155                 160

Ser Val His Trp Tyr Gln Gln Lys Pro Gly Gln Ala Pro Val Val Val
                165                 170                 175

Val His Asp Asp Ser Asp Arg Pro Ser Gly Ile Pro Glu Arg Phe Ser
        180                 185                 190

Gly Ser Asn Ser Gly Thr Thr Ala Thr Leu Thr Ile Ile Arg Val Glu
        195                 200                 205

Ala Gly Asp Glu Ala Asp Tyr Tyr Cys Gln Ala Trp Asp Ser Ile Ser
210                 215                 220

Glu Glu Val Val Phe Gly Gly Gly Thr Lys Leu Thr Val Leu
225                 230                 235
```

<210> SEQ ID NO 31
<211> LENGTH: 242
<212> TYPE: PRT
<213> ORGANISM: Artificial
<220> FEATURE:
<223> OTHER INFORMATION: Single chain antibody

<400> SEQUENCE: 31

```
Gln Val Gln Leu Gln Glu Ser Gly Gly Gly Leu Val Lys Pro Gly Gly
1               5                   10                  15

Pro Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ser Thr Leu Ser Arg Ser Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Phe Gln Met Asn Ser Leu Arg Ala Glu Asp Thr Ala Val Tyr Tyr Cys
                85                  90                  95

Ala Ser Ile Ala Val Ala Gly Asn Tyr Phe Glu Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ser Tyr Val Leu Thr Gln Asp Pro Ala Val
        130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Arg Pro Gly Gln Ala
                165                 170                 175

Pro Leu Leu Val Ile Tyr Gly Lys Asn Asn Arg Pro Ser Gly Ile Pro
            180                 185                 190

Asp Arg Phe Ser Gly Ser Asn Ser Gly Ser Thr Ala Thr Leu Thr Ile
        195                 200                 205

Ser Arg Val Glu Ala Gly Asp Glu Gly Asp Tyr Tyr Cys Gln Val Trp
210                 215                 220

Asp Ser Ile Asn Glu Gln Val Val Phe Gly Gly Gly Thr Lys Val Thr
225                 230                 235                 240

Val Leu
```

```
<210> SEQ ID NO 32
<211> LENGTH: 243
<212> TYPE: PRT
<213> ORGANISM: Artificial
<220> FEATURE:
<223> OTHER INFORMATION: Single chain antibody

<400> SEQUENCE: 32

Gln Val Gln Leu Gln Glu Ser Gly Gly Gly Leu Val Lys Pro Gly Glu
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Ala Tyr Ile Arg Tyr Asp Gly Ser Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Phe Tyr Tyr Cys
                85                  90                  95

Ala Arg Leu Ile Ala Glu Ala Glu Gly Trp Phe Asp Pro Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asn Phe Met Leu Thr Gln Pro Pro Ser
    130                 135                 140

Val Ser Val Ala Pro Gly Lys Thr Ala Arg Ile Thr Cys Gly Gly Asn
145                 150                 155                 160

Asn Ile Gly Ser Lys Ser Val Tyr Trp Tyr Gln Gln Lys Pro Gly Gln
                165                 170                 175

Ala Pro Val Leu Val Val Tyr Asp Asp Ser Asp Arg Pro Ser Gly Ile
            180                 185                 190

Pro Glu Arg Phe Ser Gly Ser Asn Ser Gly Asn Thr Ala Thr Leu Thr
        195                 200                 205

Ile Ser Arg Val Glu Ala Gly Asp Glu Ala Asp Tyr Tyr Cys Gln Val
    210                 215                 220

Trp Asp Ser Ser Asp His Val Val Phe Gly Gly Gly Thr Lys Val
225                 230                 235                 240

Thr Val Leu

<210> SEQ ID NO 33
<211> LENGTH: 241
<212> TYPE: PRT
<213> ORGANISM: Artificial
<220> FEATURE:
<223> OTHER INFORMATION: Single chain antibody

<400> SEQUENCE: 33

Gln Val Gln Leu Leu Gln Ser Ala Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Gly Ser Thr Asn Tyr Ala Asp Ser Val
    50                  55                  60
```

```
Lys Gly Arg Phe Thr Ile Ser Arg Asp Ser Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Lys Asp Tyr Gly Ser Gly Trp Tyr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Glu Arg Pro Gly Gln Ala Pro
                165                 170                 175

Leu Leu Val Ile Tyr Gly Arg Asn Glu Arg Pro Ser Gly Ile Pro Asp
            180                 185                 190

Arg Phe Ser Ala Ser Ser Ser Gly Asn Thr Ala Ser Leu Thr Ile Thr
        195                 200                 205

Gly Ala Gln Ala Glu Asp Glu Ala Asp Tyr Tyr Cys Gln Val Trp Asp
210                 215                 220

Ser Phe Asn Glu Gln Val Val Phe Gly Gly Gly Thr Lys Leu Thr Val
225                 230                 235                 240

Leu

<210> SEQ ID NO 34
<211> LENGTH: 245
<212> TYPE: PRT
<213> ORGANISM: Artificial
<220> FEATURE:
<223> OTHER INFORMATION: Single chain antibody

<400> SEQUENCE: 34

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val His Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Tyr Tyr Gly Phe Trp Ser Gly Tyr Tyr Asp Tyr Leu Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Ser Glu Leu Thr Gln Asp Pro
    130                 135                 140

Ala Val Ser Val Gly Leu Gly Gln Thr Val Thr Ile Thr Cys Gln Gly
145                 150                 155                 160

Asp Ser Leu Arg Ser Tyr Tyr Ala Asn Trp Tyr Gln Gln Lys Pro Gly
                165                 170                 175

Gln Ala Pro Ile Leu Val Ile Tyr Gly Glu Asn Asn Arg Pro Ser Gly
```

```
                180             185             190
Ile Pro Asp Arg Phe Ser Gly Ser Ser Gly Asn Thr Ala Ser Leu
            195             200             205

Thr Ile Thr Gly Ala Gln Ala Glu Asp Glu Ala Asp Tyr Tyr Cys His
        210             215             220

Ser Arg Asp Ser Ser Gly Thr His Leu Arg Val Phe Gly Gly Gly Thr
225             230             235             240

Lys Leu Thr Val Leu
            245

<210> SEQ ID NO 35
<211> LENGTH: 244
<212> TYPE: PRT
<213> ORGANISM: Artificial
<220> FEATURE:
<223> OTHER INFORMATION: Single chain antibody

<400> SEQUENCE: 35

Gln Val Gln Leu Leu Glu Ser Gly Gly Val Val Gln Pro Gly Thr
1               5                   10                  15

Ser Leu Arg Leu Ser Cys Ala Ala Ser Gly Phe Thr Phe Ser Asn Tyr
            20                  25                  30

Ala Ile Asn Trp Val Arg Gln Ala Ala Gly Lys Gly Leu Glu Trp Val
        35                  40                  45

Ser Gly Ile Ser Gly Ser Gly Val Ser Thr Ser Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asn Gly Gly Gly Pro Glu Tyr Leu Gln His Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Pro Glu Asp Glu Ala Asp Tyr Tyr Cys Gly
    210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 36
<211> LENGTH: 238
<212> TYPE: PRT
<213> ORGANISM: Artificial
<220> FEATURE:
<223> OTHER INFORMATION: Single chain antibody
```

-continued

```
<400> SEQUENCE: 36

Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Tyr Ser Gly Ser Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Ser Leu
                165                 170                 175

Val Ile Tyr Gly Glu Asn Ser Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asn Glu Ala Asp Tyr Tyr Cys Gln Ala Trp Asp Ser Ser
    210                 215                 220

Thr Ala Val Val Phe Gly Gly Gly Thr Lys Leu Thr Val Leu
225                 230                 235

<210> SEQ ID NO 37
<211> LENGTH: 238
<212> TYPE: PRT
<213> ORGANISM: Artificial
<220> FEATURE:
<223> OTHER INFORMATION: Single chain antibody

<400> SEQUENCE: 37

Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Tyr Ser Gly Ser His Trp Gly Gln Gly Thr Leu Val
            100                 105                 110

Thr Val Ser Ser Gly Gly Gly Gly Ser Gly Gly Gly Gly Ser Gly Gly
```

```
                    115                 120                 125
Gly Gly Ser Ser Ser Glu Leu Thr Gln Asp Pro Ala Val Ser Val Ala
        130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Ser Leu
                165                 170                 175

Val Ile Tyr Gly Glu Asn Ser Arg Pro Ser Gly Ile Pro Asp Arg Phe
            180                 185                 190

Ser Gly Ser Ser Ser Gly Asn Thr Ala Ser Leu Thr Ile Thr Gly Ala
                195                 200                 205

Gln Ala Glu Asn Glu Ala Asp Tyr Tyr Cys Gln Ala Trp Asp Ser Ser
        210                 215                 220

Thr Ala Val Val Phe Gly Gly Gly Thr Lys Leu Thr Val Leu
225                 230                 235
```

<210> SEQ ID NO 38
<211> LENGTH: 244
<212> TYPE: PRT
<213> ORGANISM: Artificial
<220> FEATURE:
<223> OTHER INFORMATION: Single chain antibody

<400> SEQUENCE: 38

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Pro Ile Tyr Asp Ser Ser Gly Tyr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Ser Thr Leu Ser Ala Ser Ile Gly Asp Arg Val Thr Ile Thr Cys
145                 150                 155                 160

Arg Ala Ser Glu Gly Ile Tyr His Trp Leu Ala Trp Tyr Gln Gln Lys
                165                 170                 175

Pro Gly Lys Ala Pro Lys Leu Leu Ile Tyr Lys Ala Ser Ser Leu Ala
            180                 185                 190

Ser Gly Ala Pro Ser Arg Phe Ser Gly Ser Gly Ser Gly Thr Asp Phe
        195                 200                 205

Thr Leu Thr Ile Ser Ser Leu Gln Pro Asp Asp Phe Ala Thr Tyr Tyr
    210                 215                 220

Cys Gln Gln Tyr His Thr Ile Ser Arg Thr Phe Gly Pro Gly Thr Lys
225                 230                 235                 240

Val Asp Ile Lys
```

<210> SEQ ID NO 39
<211> LENGTH: 244
<212> TYPE: PRT
<213> ORGANISM: Artificial
<220> FEATURE:
<223> OTHER INFORMATION: Single chain antibody

<400> SEQUENCE: 39

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Val Arg Pro Ser Asp Ser Gly Trp Ser Phe Glu His Trp Gly Gln Gly
            100                 105                 110

Thr Leu Val Pro Val Ser Ser Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Pro Glu Asp Glu Ala Asp Tyr Tyr Cys Gly
    210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 40
<211> LENGTH: 245
<212> TYPE: PRT
<213> ORGANISM: Artificial
<220> FEATURE:
<223> OTHER INFORMATION: Single chain antibody

<400> SEQUENCE: 40

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Gly Asp Arg Ser Tyr Gly Ala Glu Tyr Phe Gln His Trp Gly
            100                 105                 110

Gln Gly Thr Leu Val Thr Val Ser Ser Gly Gly Gly Ser Gly Gly Gly
            115                 120                 125

Gly Gly Ser Gly Gly Gly Ser Ser Glu Leu Thr Gln Asp Pro
130                 135                 140

Ala Val Ser Val Ala Ser Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Leu Leu Val Ile Tyr Gly Lys Asn Ile Arg Pro Ser Gly
                180                 185                 190

Ile Pro Asp Arg Phe Ser Gly Ser Thr Ser Gly Asn Ser Ala Ser Leu
            195                 200                 205

Thr Ile Thr Gly Ala Gln Ala Glu Asp Glu Ala Asp Tyr Tyr Cys Asn
        210                 215                 220

Ser Arg Asp Ser Gly Asn Arg Asn Trp Val Phe Gly Gly Gly Thr
225                 230                 235                 240

Lys Leu Thr Val Leu
                245

<210> SEQ ID NO 41
<211> LENGTH: 246
<212> TYPE: PRT
<213> ORGANISM: Artificial
<220> FEATURE:
<223> OTHER INFORMATION: Single chain antibody

<400> SEQUENCE: 41

Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Ser Ser Ser Tyr
                20                  25                  30

Ala Met His Trp Val Arg Gln Ala Pro Gly Lys Gly Leu Glu Tyr Val
            35                  40                  45

Ser Ala Ile Gly Gly Asn Gly Gly Thr Tyr Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Glu Gly Glu Gln Trp Leu Val Tyr Arg Tyr Tyr Tyr Gly Met Asp
            100                 105                 110

Val Trp Gly Gln Gly Thr Thr Val Thr Val Ser Ser Gly Gly Gly Gly
            115                 120                 125

Ser Gly Gly Gly Gly Ser Gly Gly Gly Ser Ser Glu Leu Thr
        130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Ala Ser Trp Tyr Gln Gln
                165                 170                 175
```

```
Lys Pro Gly Gln Ala Pro Ser Leu Val Ile Tyr Gly Glu Asn Ser Arg
            180                 185                 190

Pro Ser Gly Ile Pro Asp Arg Phe Ser Gly Ser Ser Gly Asn Thr
        195                 200                 205

Ala Ser Leu Thr Ile Thr Gly Ala Gln Ala Glu Asn Glu Ala Asp Tyr
        210                 215                 220

Tyr Cys Gln Ala Trp Asp Ser Ser Thr Ala Val Val Phe Gly Gly Gly
225                 230                 235                 240

Thr Lys Leu Thr Val Leu
            245

<210> SEQ ID NO 42
<211> LENGTH: 250
<212> TYPE: PRT
<213> ORGANISM: Artificial
<220> FEATURE:
<223> OTHER INFORMATION: Single chain antibody

<400> SEQUENCE: 42

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Tyr Ser Ser Asn Trp Phe Ser Tyr Tyr Tyr Tyr
            100                 105                 110

Gly Met Asp Val Trp Gly Gln Gly Thr Thr Val Thr Val Ser Ser Gly
        115                 120                 125

Gly Gly Gly Ser Gly Gly Gly Gly Ser Gly Gly Gly Gly Ser Asn Phe
    130                 135                 140

Met Leu Thr Gln Pro Pro Ser Val Ser Val Ala Pro Gly Lys Thr Ala
145                 150                 155                 160

Arg Ile Thr Cys Gly Gly Asn Asn Ile Gly Ser Lys Ser Val Tyr Trp
                165                 170                 175

Tyr Gln Gln Lys Pro Gly Gln Ala Pro Val Leu Val Val Tyr Asp Asp
            180                 185                 190

Ser Asp Arg Pro Ser Gly Ile Pro Glu Arg Phe Ser Gly Ser Asn Ser
        195                 200                 205

Gly Asn Thr Ala Thr Leu Thr Ile Ser Arg Val Glu Ala Gly Asp Glu
    210                 215                 220

Ala Asp Tyr Tyr Cys Gln Val Trp Asp Ser Ser Ser Asp His Val Val
225                 230                 235                 240

Phe Gly Gly Gly Thr Lys Val Thr Val Leu
            245                 250
```

INTERNALIZING HUMAN MONOCLONAL ANTIBODIES TARGETING PROSTATE AND OTHER CANCER CELLS

CROSS-REFERENCE TO RELATED APPLICATIONS

This application claims benefit of and priority to U.S. Ser. No. 61/785,118, filed Mar. 14, 2013, which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under grant No. R01 CA118919, awarded by the National Institutes of Health. The government has certain rights in the invention.

BACKGROUND

Due to ease of accessibility, tumor cell surface antigens are invaluable targets for therapeutic development. The epitope space at the cell surface is highly complex. Relevant antigens may include glycosylated proteins and other post-translationally modified products that may not be readily predicted from studies of genomic copy number or mRNA expression levels (Liu et al. (2004) *Cancer Res.* 64: 704-710; Kobata and Amano (2005) *Immunol. Cell Biol.* 83: 429-439; Birkle et al. (2003) *Biochimie* (Paris) 85: 455-463; Hakomori (2001) *Adv. Exp. Med. Biol.* 491: 369-402; Hanisch, F. G. (2001) O-Glycosylation of the mucin type. *Biol. Chem.* 382, 143-149; Ugorski and Laskowska (2002) *Acta Biochim. Pol.* 49: 303-311).

Identification of tumor cell surface epitopes allows the production of antibodies to achieve specific binding to neoplastic cells, an ability that can be utilized in applications such as induction of antibody-dependent cell cytotoxicity (see, e.g., Clynes et al. (2000) *Nat. Med.* 6: 443-446), or inhibition of signaling pathways involved in tumor cell migration, growth, and survival (see, e.g., McWhirter et al. (2006) *Proc. Natl. Acad. Sci.*, USA, 103: 1041-1046; Fuh et al. (2006) *J. Biol. Chem.* 281: 6625-6631). In addition, antibodies targeting internalizing tumor epitopes can be exploited to achieve efficient and specific intracellular delivery of cytotoxins, cytostatic agents, chemotherapeutic drugs and/or other tumor-modulating agents (see, e.g., Liu et al. (2004) *Cancer Res.* 64: 704-710; Nielsen et al. (2002) *Biochim. Biophys. Acta* 1591: 109-118; Pirollo et al. (2006) *Hum. Gene Ther.* 17: 117-124; Song et al. (2005) *Nat. Biotechnol.* 23:709-717; Liu et al. (2002) *J. Mol. Biol.* 315: 1063-1073).

Phage antibody display has been widely used to develop cancer-specific antibodies (see, e.g., Liu et al. (2004) *Cancer Res.* 64: 704-710; Liu and Marks (2000) *Anal. Biochem.* 286: 119-128; 15. Marks et al. (1992) *Biotechnology* (N.Y.) 10: 779-783; Marks et al. (1991) *J. Mol. Biol.* 222: 581-597; Marks et al. (1992) *J. Biol. Chem.* 267: 16007-16010; Sharon et al. (2005) *J. Cell. Biochem.* 96: 305-313; Silacci et al. (2005) *Proteomics* 5: 2340-2350; Gao et al. (2003) *J. Immunol. Methods* 274: 185-197; Lekkerkerker and Logtenberg (1999) *J. Immunol. Meth.*, 231: 53-63; de Kruif et al. (1995) *Proc. Natl. Acad. Sci.*, USA, 92: 3938-3942; Pini et al. (1998) *J. Biol. Chem.* 273: 21 769-21 776). A combinatorial phage antibody library serves as a source of random shape repertoire that can be used to probe neoplastic variations on the surface of cancer cells (see, e.g., Liu et al. (2004) *Cancer Res.* 64: 704-710; Geuijen et al. (2005) *Eur. J. Cancer* 41: 178-187; Poul et al. (2000) *J. Mol. Biol.* 301: 1149-1161; Cai and Garen (1995) *Proc. Natl. Acad. Sci.*, USA, 92: 6537-6541). Selecting phage antibody libraries directly on cancer cell lines enables the identification of tumor-targeting antibodies without prior knowledge of target antigens see, e.g., (Liu et al. (2004) *Cancer Res.* 64: 704-710; Gao et al. (2003) *J. Immunol. Methods* 274: 185-197; Geuijen et al. (2005) *Eur. J. Cancer* 41: 178-187; Poul et al. (2000) *J. Mol. Biol.* 301: 1149-1161).

Although numerous antibodies have been found by this approach, the screening process against cell lines does not provide an ideal picture as to how specific these antibodies will be to actual cancer cells in patient populations. Nor does it necessarily provide an indication of whether or not the antibodies will internalize in vivo.

SUMMARY

In various aspects, the invention(s) contemplated herein may include, but need not be limited to, any one or more of the following embodiments:

Embodiment 1

An isolated antibody that specifically binds and is internalized into a prostate cancer cell, wherein: said antibody is an antibody that specifically binds cells that express or overexpress a CD46, wherein said antibody specifically binds sushi domain 1 of said CD46; and said antibody does not comprise VH CDR1, VH CDR2, VH CDR3, VL CDR1, VL CDR2, and VL CDR3 of the following antibodies: 3051.1, G12FC3, M6c42b, 4F3YW, M40pr146, UA20, UA8, 585I141, 585I141.1, 585I156, 3076, 3051, M49R, RCI-14, II79_4, II79_3, T5II-4B.1, T5II-4B.2, RCI-11, RCI-20, CI-11A, CI-14A, S95-2, and mPA7.

Embodiment 2

The antibody of embodiment 1, wherein said antibody binds to at least a portion of the sushi domain 1 including the amino acid sequence KPYYEIGERVDYKCKKGYFYIP-PLATHTICDR (SEQ ID NO:1).

Embodiment 3

The antibody according to any one of embodiments 1-2, wherein said cells that express or overexpress a CD46 are prostate cancer cells.

Embodiment 4

The antibody of embodiment 3, wherein said antibody bind cells of a cell line selected from the group consisting of DU145 cells, PC3 cells, and LnCaP cells.

Embodiment 5

The antibody according to any one of embodiments 1-4, wherein said antibody binds to a prostate tumor cell with an affinity (KD) of at least about 5 nM when measured on live prostate tumor cells by FACS.

Embodiment 6

The antibody of embodiment 5, wherein said antibody binds to a prostate tumor cell with an affinity (KD) of at least about 3 nM when measured on live prostate tumor cells by FACS.

Embodiment 7

The antibody according to any one of embodiments 1-6, wherein said antibody is a substantially intact immunoglobulin.

Embodiment 8

The antibody of embodiment 7, wherein said antibody includes an IgA, IgE, or IgG.

Embodiment 9

The antibody of embodiment 7, wherein said antibody includes an IgG1.

Embodiment 10

The antibody according to any one of embodiments 1-6, wherein said antibody is an antibody fragment that specifically binds cells that express or overexpress a CD46.

Embodiment 11

The antibody of embodiment 10, wherein said antibody is an antibody fragment selected from the group consisting of Fv, Fab, (Fab')2, (Fab')3, IgGΔCH2, and a minibody.

Embodiment 12

The antibody according to any one of embodiments 1-6, wherein said antibody is a single chain antibody.

Embodiment 13

The antibody of embodiment 12, wherein the VL region of said antibody is attached to the VH region of said antibody by an amino acid linker ranging in length from about 3 amino acids up to about 15 amino acids.

Embodiment 14

The antibody of embodiment 12, wherein the VL region of said antibody is attached to the VH region of said antibody by an amino acid linker selected from the group consisting of GGGGS GGGGS GGGGS (SEQ ID NO:2), GGGGS GGGGS (SEQ ID NO:3), GGGGS (SEQ ID NO:4), GS GGGGS GGGGS GGS GGGGS (SEQ ID NO:5), SGGGGS (SEQ ID NO:6), GGGS (SEQ ID NO:7), VPGV (SEQ ID NO:8), VPGVG (SEQ ID NO:9), GVPGVG (SEQ ID NO:10), GVG VP GVG (SEQ ID NO:11), VP GVG VP GVG (SEQ ID NO:12), GGSSRSS (SEQ ID NO:13), and GGSSRSSSSGGGGSGGGG (SEQ ID NO:14).

Embodiment 15

The antibody according to any one of embodiments 1-14, wherein said antibody includes VH CDR1, and/or VH CDR2, and/or VH CDR3 of the 2B10 antibody.

Embodiment 16

The antibody according to any one of embodiments 1-14, wherein said antibody includes VL CDR1, and/or VL CDR2, and/or VL CDR3 of the 2B10 antibody.

Embodiment 17

The antibody according to any one of embodiments 1-14, wherein said antibody includes VH CDR1, and VH CDR2, and VH CDR3 of the 2B10 antibody.

Embodiment 18

The antibody according to any one of embodiments 1-14, wherein said antibody includes VL CDR1, and VL CDR2, and VL CDR3 of the 2B10 antibody.

Embodiment 19

The antibody according to any one of embodiments 1-14, wherein said antibody includes the variable light (VL) chain of the 2B10 antibody.

Embodiment 20

The antibody according to any one of embodiments 1-14, wherein said antibody includes the variable heavy (VH) chain of the 2B10 antibody.

Embodiment 21

The antibody according to any one of embodiments 1-14, wherein said antibody includes the variable light (VL) chain of the 2B10 antibody and the variable heavy (VH) chain of the 2B10 antibody.

Embodiment 22

The antibody of embodiment 1, wherein said antibody is a human 2B10 scFv.

Embodiment 23

The antibody of embodiment 1, wherein said antibody is a human 2B10 IgG.

Embodiment 24

A immunoconjugate including an antibody according to any one of embodiments 1-23 attached to an effector wherein said effector is selected from the group consisting of a second antibody, a detectable label, a cytotoxin or cytostatic agent, a liposome containing a drug, a radionuclide, a drug, a prodrug, a viral particle, a cytokine, and a chelate.

Embodiment 25

The immunoconjugate of embodiment 24, wherein said antibody is attached to a cytotoxin.

Embodiment 26

The immunoconjugate of embodiment 25, wherein said antibody is attached to a cytotoxin selected from the group consisting of a *Diphtheria* toxin, a *Pseudomonas* exotoxin, a ricin, an abrin, saporin, and a thymidine kinase.

Embodiment 27

The immunoconjugate of embodiment 24, wherein said antibody is attached to a cytotoxic and/or cytostatic drug.

Embodiment 28

The immunoconjugate of embodiment 25, wherein said antibody is attached directly or through a linker to one or more of the following: said drug a lipid or liposome containing said drug; a polymeric drug carrier including said drug; and a nanoparticle drug carrier including said drug.

Embodiment 29

The immunoconjugate according to any one of embodiments 27-28, wherein said drug is an anti-cancer drug.

Embodiment 30

The immunoconjugate according to any one of embodiments 27-28, wherein said drug is selected from the group consisting of auristatin, dolastatin, colchicine, combretastatin, and mTOR/PI3K inhibitors.

Embodiment 31

The immunoconjugate according to any one of embodiments 27-28, wherein said drug is monomethyl auristatin F.

Embodiment 32

The immunoconjugate according to any one of embodiments 27-28, wherein said drug is selected from the group consisting of fluorouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1,-(2-chloroethyl)-3-cyclohexyl-Initrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, and vinflunine.

Embodiment 33

The immunoconjugate according to any one of embodiments 27-28, wherein said drug is selected from the group consisting of carboplatin, cisplatin, cyclophosphamide, docetaxel, doxorubicin, erlotinib, etoposide, gemcitabine, imatinib mesylate, irinotecan, methotrexate, sorafinib, sunitinib, topotecan, vinblastine, and vincristine.

Embodiment 34

The immunoconjugate according to any one of embodiments 27-28, wherein said drug is selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 35

The immunoconjugate of embodiment 24, wherein said antibody is attached to a chelate including an isotope selected from the group consisting of 99Tc, 203Pb, 67Ga, 68Ga, 72As, 111In, 113In, 97Ru, 62Cu, 641Cu, 52Fe, 52Mn, 51Cr, 186, Re, 188Re, 77As, 90Y, 67Cu, 169Er, 121Sn, 127Te, 142Pr, 143Pr, 198Au, 199Au, 161Tb, 109Pd, 165Dy, 149 Pm, 151 Pm, 153Sm, 157Gd, 159Gd, 166Ho, 172Tm, 169Yb, 175Yb, 177Lu, 105Rh, and 111Ag.

Embodiment 36

The immunoconjugate of embodiment 24, wherein said antibody is attached to an alpha emitter.

Embodiment 37

The immunoconjugate of embodiment 36, wherein said alpha emitter is bismuth 213.

Embodiment 38

The immunoconjugate of embodiment 24, wherein said antibody is attached to a lipid or a liposome complexed with or containing an anti-cancer drug.

Embodiment 39

The immunoconjugate of embodiment 24, wherein said antibody is attached to a detectable label.

Embodiment 40

The immunoconjugate of embodiment 39, wherein said antibody is attached to a detectable label selected from the group consisting of a radioactive label, a radioopaque label, an MRI label, and a PET label.

Embodiment 41

A pharmaceutical formulation said formulation including: a pharmaceutically acceptable excipient and an antibody according to any one of embodiments 1-23; and/or a pharmaceutically acceptable excipient and a immunoconjugate according to any one of embodiments 24-40.

Embodiment 42

The pharmaceutical formulation of embodiment 41, wherein said formulation is a unit dosage formulation.

Embodiment 43

The formulation according to any one of embodiments 41-42, wherein said formulation is formulated for administration via a route selected from the group consisting of oral administration, nasal administration, rectal administration, intraperitoneal injection, intravascular injection, subcutaneous injection, transcutaneous administration, and intramuscular injection.

Embodiment 44

A method of inhibiting the growth and/or proliferation of a cancer cell that expresses or overexpresses CD46, said method including: contacting said cancer cell with a immunoconjugate including an antibody according to any one of embodiments 1-23 attached to an effector that has cytostatic and/or cytotoxic activity.

Embodiment 45

The method of embodiment 44, wherein said effector includes one or more of the following: a cytotoxic and/or cytostatic drug; a lipid or liposome containing a cytotoxic and/or cytostatic drug; a polymeric drug carrier including a cytotoxic and/or cytostatic drug; and a nanoparticle drug carrier including a cytotoxic and/or cytostatic drug.

Embodiment 46

The method of embodiment 44, wherein said drug is an anti-cancer drug.

Embodiment 47

The method according to any one of embodiments 44-46, wherein said drug is selected from the group consisting of auristatin, dolastatin, colchicine, combretastatin, and mTOR/PI3K inhibitors.

Embodiment 48

The method according to any one of embodiments 44-46, wherein said drug is monomethyl auristatin F.

Embodiment 49

The method according to any one of embodiments 44-46, wherein said drug is selected from the group consisting of fluorouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1,-(2-chloroethyl)-3-cyclohexyl-Initrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, and vinflunine.

Embodiment 50

The method according to any one of embodiments 44-46, wherein said drug is selected from the group consisting of carboplatin, cisplatin, cyclophosphamide, docetaxel, doxorubicin, erlotinib, etoposide, gemcitabine, imatinib mesylate, irinotecan, methotrexate, sorafinib, sunitinib, topotecan, vinblastine, and vincristine.

Embodiment 51

The method according to any one of embodiments 44-46, wherein said drug is selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 52

The method of embodiment 44, wherein said effector includes a cytotoxin.

Embodiment 53

The method of embodiment 52, wherein said cytotoxin is selected from the group consisting of *Diphtheria* toxin, *Pseudomonas* exotoxin, ricin, abrin, saporin, and thymidine kinase.

Embodiment 54

The method of embodiment 44, wherein said effector includes a radionuclide.

Embodiment 55

The method of embodiment 44, wherein said effector includes an anti-cancer drug.

Embodiment 56

The method of embodiment 55, wherein said anticancer drug is conjugated to said antibody.

Embodiment 57

The method of embodiment 55, wherein said anticancer drug is contained in a lipid or liposome attached to said antibody.

Embodiment 58

The method according to any one of embodiments 44-57, wherein said cancer cell is selected from the group consisting of ovarian cancer, breast cancer, lung cancer, prostate cancer, colon cancer, kidney cancer, pancreatic cancer, mesothelioma, lymphoma, liver cancer, urothelial cancer, stomach cancer, and cervical cancer.

Embodiment 59

The method according to any one of embodiments 44-57, wherein said cancer cell is a prostate cancer cell.

Embodiment 60

The method according to any one of embodiments 44-59, wherein said cell is a metastatic cell.

Embodiment 61

The method according to any one of embodiments 44-59, wherein said cell is a solid tumor cell.

Embodiment 62

The method according to any one of embodiments 44-61, wherein said immunoconjugate is administered in a pharmaceutical composition including a pharmaceutical acceptable carrier.

Embodiment 63

The method according to any one of embodiments 44-62, wherein said administering includes administering to a human.

Embodiment 64

The method according to any one of embodiments 44-62, wherein said administering includes administering to a non-human mammal.

Embodiment 65

The method according to any one of embodiments 44-64, wherein said administering includes administering parenterally.

Embodiment 66

The method according to any one of embodiments 44-64, wherein said administering includes administering into a tumor or a surgical site.

Embodiment 67

The method according to any one of embodiments 44-66, wherein said immunoconjugate is administered as an adjunct therapy to surgery and/or radiotherapy.

Embodiment 68

The method according to any one of embodiments 44-66, wherein said immunoconjugate is administered in conjunction with another anti-cancer drug and/or a hormone.

Embodiment 69

A method of detecting a cancer cell, said method including: contacting said cancer cell with a immunoconjugate including an antibody according to any one of embodiments 1-23 attached to a detectable label; and detecting the presence and/or location of said detectable label where the presence and/or location is an indicator of the location and/or presence of a prostate cancer cell.

Embodiment 70

The method of embodiment 69, wherein said label includes a label selected from the group consisting of a radioactive label, a radioopaque label, an MRI label, and a PET label.

Embodiment 71

The method of embodiment 69, wherein said detectable label is selected from the group consisting of a gamma-emitter, a positron-emitter, an x-ray emitter, an alpha emitter, and a fluorescence-emitter.

Embodiment 72

The method according to any one of embodiments 69-71, wherein said cancer cell is selected from the group consisting of ovarian cancer, breast cancer, lung cancer, prostate cancer, colon cancer, kidney cancer, pancreatic cancer, mesothelioma, lymphoma, liver cancer, urothelial cancer, stomach cancer, and cervical cancer.

Embodiment 73

The method according to any one of embodiments 69-72, wherein said contacting includes administering said immunoconjugate to a non-human mammal.

Embodiment 74

The method according to any one of embodiments 69-72, wherein said contacting includes administering said immunoconjugate to a human.

Embodiment 75

The method according to any one of embodiments 73-74, wherein said detecting includes detecting said label in vivo.

Embodiment 76

The method of embodiment 75, wherein said detecting includes using a detection method selected from the group consisting of X-ray, PET, MRI, and CAT.

Embodiment 77

A nucleic acid encoding an antibody or a fragment of an antibody according to any of embodiments 1-23.

Embodiment 78

An expression vector including the nucleic acid of embodiment 77.

Embodiment 79

A cell including the expression vector of embodiment 78.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10):1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphosphoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) Proc. Nat. Acad. Sci. USA, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) Protein Eng. 8: 1323-1331).

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The phrase "inhibition of proliferation of a cell expressing CD46" as used herein, refers to the ability of an anti-CD46 CPP1 antibody or immunoconjugate described herein decrease, preferably to statistically significantly decrease proliferation of a cell expressing CD46 relative to the proliferation in the absence of the antibody or immunoconjugate. In one embodiment, the proliferation of a cell expressing CD46 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof or an immunoconjugate described herein, relative to the proliferation measured in the absence of the antibody or antigen binding portion thereof or immunoconjugate (control). Cellular proliferation can be assayed using art recognized techniques which measure rate of cell division, the fraction of cells within a cell population undergoing cell division, and/or rate of cell loss from a cell population due to terminal differentiation or cell death (e.g., using a cell titer glow assay or thymidine incorporation).

The phrase "inhibition of the migration of cells expressing CD46" as used herein, refers to the ability of an anti-CD46 CPP1 antibody or an antigen-binding portion thereof or an immunoconjugate described herein to decrease, preferably to statistically significantly decrease the migration of a cell expressing CD46 relative to the migration of the cell in the absence of the antibody. In one embodiment, the migration of a cell expressing CD46 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof or immunoconjugate thereof, relative to cell migration measured in the absence of the antibody or antigen binding portion thereof or immunoconjugate thereof (control). Cell migration can be assayed using art recognized techniques.

The term "antigen-binding portion" of an antibody (or simply "antibody portion"), as used herein, refers to one or more fragments of an antibody that retain the ability to specifically bind to an antigen (e.g., CD46 CPP1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (see, e.g., Ward et al. (1989) Nature 341: 544-546), which consists of a $V_H$ domain; (vii) a dAb which consists of a $V_H$ or a $V_L$ domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, can be coded for by separate genes, they can be joined, using recombinant methods, by a synthetic linker that enables them to be made as a single protein chain in which the $V_L$ and V-regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al. (1975) Nature, 256: 495, a transgenic animal, as described by, for example, (see e.g., Lonberg, et al. (1994) Nature 368(6474): 856-859), recombinant DNA methods (see, e.g., U.S. Pat. No. 4,816,567), or using phage antibody libraries using the techniques described in, for example, Clackson et al. (1991) Nature, 352: 624-628, and Marks et al. (1991) J. Mol. Biol., 222: 581-597. Monoclonal antibodies include chimeric antibodies, human antibodies and humanized antibodies and may occur naturally or be recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline V- and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue which is not encoded by the human germline immunoglobulin sequence. Typically, the human antibody can have up to twenty positions replaced with amino acid residues which are not part of the human germline immunoglobulin sequence. In a particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

As used herein, a "heterologous antibody" is defined in relation to the transgenic non-human organism or plant producing such an antibody.

An "isolated antibody," as used herein, is intended to refer to an antibody that is substantially free of other antibodies having different antigenic specificities (e.g., an isolated antibody that specifically binds to CD46 CPP1 is substantially free of antibodies that specifically bind antigens other than CD46 CPP1). In addition, an isolated antibody is typically substantially free of other cellular material and/or chemicals. In one embodiment, a combination of "isolated" monoclonal antibodies having different CD46 binding specificities are combined in a well defined composition.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, a monoclonal antibody of the invention is of the IgG1 isotype. In other embodiments, a monoclonal antibody of the invention is of the IgG2 isotype.

An "antigen" is an entity (e.g., a proteinaceous entity or peptide) to which an antibody or antigen-binding portion thereof binds. In various embodiments of the present invention, an antigen is CD46 CPP1, e.g., as presented on a cell (e.g., a CD46 positive cancer cell).

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

Also contemplated herein are antibodies that bind the same or an overlapping epitope as the 2B10 antibody described. Antibodies that recognize the same epitope can be identified using routine techniques such as an immunoassay, for example, by showing the ability of one antibody to block the binding of another antibody to a target antigen, i.e., a competitive binding assay. Competitive binding is determined in an assay in which the immunoglobulin under test inhibits specific binding of a reference antibody to a common antigen, such as CD46 CPP1, more preferably the epitope of SEQ ID NO:1. Numerous types of competitive binding assays are known, for example: solid phase direct or indirect radioimmunoassay (RIA), solid phase direct or indirect enzyme immunoassay (EIA), sandwich competition assay (see, e.g., Stahli et al. (1983) *Meth. Enzymol.,* 9: 242); solid phase direct biotin-avidin EIA (see Kirkland et al., (1986) *J. Immunol.* 137: 3614); solid phase direct labeled assay, solid phase direct labeled sandwich assay (see, e.g., Harlow and Lane (1988) *Antibodies: A Laboratory Manual,* Cold Spring Harbor Press); solid phase direct label RIA using, e.g., $^{125}$I label (see, e.g., Morel et al., (1988) *Mol. Immunol.* 25(1): 7); solid phase direct biotin-avidin EIA (Cheung et al. (1990) *Virology* 176: 546); and direct labeled RIA. (Moldenhauer et al. (1990) *Scand J. Immunol.* 32: 77). Typically, such an assay involves the use of purified antigen (e.g., CD46 sushi domain 1 (CPP1)) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "specifically binds," "selective binding," and "selectively binds," mean that an antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least (KD equal to or less than) $10^{-6}$ M, $10^{-7}$M, $10^{-8}$M, $10^{-9}$M, $10^{-10}$ M, or $10^{-11}$ M. Affinities greater than $10^{-9}$ M, preferably greater than $10^{-10}$ M are more preferred. Values intermediate of those set forth herein are also intended to be within the scope of the present invention and a preferred binding affinity can be indicated as a range of affinities, for example, $10^{-6}$ M to $10^{-11}$ M, preferably $10^{-7}$ M or $10^{-8}$ M to $10^{-10}$ M. An antibody that "does not exhibit significant cross-reactivity" is one that will not appreciably bind to an undesirable entity (e.g., an undesirable proteinaceous entity). For example, in one embodiment, an antibody or antigen-binding portion thereof that specifically binds to CD46 CPP1 appreciably bind that CD46 CPP1 protein but will not significantly react with other molecules and non-CD46 proteins or peptides. Specific or selective binding can be determined according to any art-recognized means for determining such binding, including, for example, according to Scatchard analysis and/or competitive binding assays.

The term "$K_D$," as used herein, is intended to refer to the dissociation equilibrium constant of a particular antibody-antigen interaction or the affinity of an antibody for an antigen. In one embodiment, the antibody or antigen binding portion thereof according to the present invention binds an antigen (e.g., CD46-CPP1) with an affinity ($K_D$) of 5 nM or better (i.e., or less) (e.g., 40 nM or 30 nM or 20 nM or 10 nM or less), as measured using a surface plasmon resonance assay or a cell binding assay. In a particular embodiment, an antibody or antigen binding portion thereof according to the present invention binds CD46 CPP1 with an affinity ($K_D$) of 5 nM or better (e.g., 4 nM, 2 nM, 1.5 nM, 1.4 nM, 1.3 nM, 1 nM or less), as measured by a surface plasmon resonance assay or a cell binding assay. In other embodiments, an antibody or antigen binding portion thereof binds an antigen (e.g., CD46 CPP1) with an affinity ($K_D$) of approximately less than $10^{-10}$ M, or $100 \times 10^{-11}$ M, or $10 \times 10^{-11}$ M, or even lower using live prostate tumor cells by FACS.

The term "$K_{off}$" as used herein, is intended to refer to the off rate constant for the dissociation of an antibody from the antibody/antigen complex.

The term "EC50," as used herein, refers to the concentration of an antibody or an antigen-binding portion thereof or an immunoconjugate described herein, that induces a response, either in an in vitro or an in vivo assay, which is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "modifying," or "modification," as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis. For example, in some embodiments, an antibody or an antigen-binding portion thereof identified using the methods of the invention can be modified, to thereby modify the binding affinity of the antibody or antigen-binding portion thereof to CD46 CPP1.

In certain embodiments "conservative amino acid substitutions" in the sequences of the anti-CD46 CPP1 antibodies described herein, i.e., nucleotide and amino acid sequence modifications that do not abrogate the binding of the antibody encoded by the nucleotide sequence or containing the amino acid sequence, to the antigen, e.g., CD46 CPP1 are contemplated. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-CD46 CPP1 antibody is preferably replaced with another amino acid residue from the same class. Methods of identifying nucleotide and amino acid conservative substitutions which do not eliminate antigen binding are well-known in the art (see, e.g., Brummell et al. (1993) *Biochem.* 32: 1180-1187; Kobayashi et al. (1999) *Protein Eng.* 12(10): 879-884; and Burks et al. (1997) *Proc. Natl. Acad. Sci. USA* 94: 412-417).

The term "non-conservative amino acid substitution" refers to the substitution of an amino acid in one class with an amino acid from another class; for example, substitution of an Ala, a class II residue, with a class III residue such as Asp, Asn, Glu, or Gln.

In another embodiment, mutations (conservative or non-conservative) can be introduced randomly along all or part of an anti-CD46 CPP1 antibody coding sequence, such as by saturation mutagenesis, and the resulting modified antibodies can be screened for binding activity.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

Similarly, the consensus sequence for the CDRs of can be derived by optimal alignment of the CDR amino acid sequences of anti-CD46 CPP1 antibodies described herein.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions.times.100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of Meyers and Miller (1989) *CABIOS*, 4: 11-17, which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) *J. Mol. Biol.* 48: 444-453 algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the contemplated herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The nucleic acid compositions described herein (e.g., nucleic acids encoding all or a portion of an anti-CD46 CPP1 antibody or immunoconjugate) while often in a native sequence (except for modified restriction sites and the like), from either cDNA, genomic or mixtures thereof may be mutated, in accordance with standard techniques to provide variant sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject (e.g., a subject in need thereof), an anti-CD46 CPP1 antibody or antigen binding portion or an immunoconjugate comprising such an antibody or antigen binding portion described herein. In certain embodiments the subject is a subject diagnosed with and/or under treatment for a CD46 positive cancer (e.g., prostate cancer) in order to prevent, cure, delay, reduce the severity of, or ameliorate one or more symptoms of the disease or disorder or recurring disease or disorder, or in order to prolong the survival of a subject beyond that expected in the absence of such treatment.

The terms "cancer" and "cancerous" refer to or describe the physiological condition in mammals that is typically characterized by unregulated cell growth. A CD46 positive cancer refers to a cancer characterized by cells that express or overexpress CD46. Illustrative CD46 cancers include, but are not limited to, ovarian cancer, breast cancer, lung cancer, prostate cancer, colon cancer, kidney cancer, and pancreatic cancer.

The term "effective amount," as used herein, refers to that amount of an anti-CD46 CPP1 antibody or an antigen binding portion thereof and/or an immunoconjugate thereof, which is sufficient to effect treatment, prognosis or diagnosis of a disease associated with the growth and/or proliferation CD46 positive cells (e.g., a CD46 positive cancer), as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 .mu.g to about 3,500 mg, about 5 .mu.g to about 3,000 mg, about 10 .mu.g to about 2,600 mg, about 20 .mu.g to about 2,575 mg, about 30 .mu.g to about 2,550 mg, about 40 .mu.g to about 2,500 mg, about 50 .mu.g to about 2,475 mg, about 100 .mu.g to about 2,450 mg, about 200 .mu.g to about 2,425 mg, about 300 .mu.g to about 2,000, about 400 .mu.g to about 1,175 mg, about 500 .mu.g to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an anti-CD46 CPP1 (preferably anti SEQ ID NO:1) antibody and/or antigen binding portion thereof, and/or immunoconjugate thereof as described herein. Dosage regiments may be adjusted to provide the optimum therapeutic response. An effective amount is also one in which any toxic or detrimental effects (i.e., side effects) of an antibody or antigen binding portion thereof are minimized and/or outweighed by the beneficial effects.

The term "patient" includes human and other mammalian subjects that receive either prophylactic or therapeutic treatment.

As used herein, the term "subject" includes any human or non-human animal. For example, the methods and compositions of the present invention can be used to treat a subject having cancer. In a particular embodiment, the subject is a human. The term "non-human animal" includes all vertebrates, e.g., mammals and non-mammals, such as non-human primates, sheep, dog, cow, chickens, amphibians, reptiles, etc.

An "effector" refers to any molecule or combination of molecules whose activity it is desired to deliver/into and/or localize at cell. Effectors include, but are not limited to, labels, cytotoxins, enzymes, growth factors, transcription factors, antibodies, drugs, etc.

The term "immunoconjugate" refers to an antibody attached to one or more effectors or to a plurality of antibodies attached to one or more effectors. The term "immunoconjugate" is intended to include effectors chemically conjugated to the antibodies as well as antibodies expresses as a fusion protein where the antibody (or a portion thereof) is directly attached or attached through a linker to a peptide effector or to an effector comprising a peptide.

BRIEF DESCRIPTION OF THE DRAWINGS

FIG. 4 illustrates antibody internalization via macropinocytosis. Confocal analysis. FITC-labeled UA20 IgG was incubated with CaP cells (Du145) along with TRITC-labeled neutral dextran, a marker for macropinocytosis. Pseudocolored channels for IgG (green), dextran (red) and nuclei (deep blue).

FIG. 8 shows sequence alignments between the amino acid sequences of the 2B10 VH domain (SEQ ID NO:5) and the UA20 VH domain (SEQ ID NO:16) and between the amino acid sequences of the 2B10 VL domain (SEQ ID NO:17) and the UA20 VL domain (SEQ ID NO:18). Heavy and light chain variable regions are compared using ClustalW. For heavy chain, the major difference is in CDR1. There are three additional mutations in framework 1. For light chain, differences are seen in CDR1.

DETAILED DESCRIPTION

Figure 1:
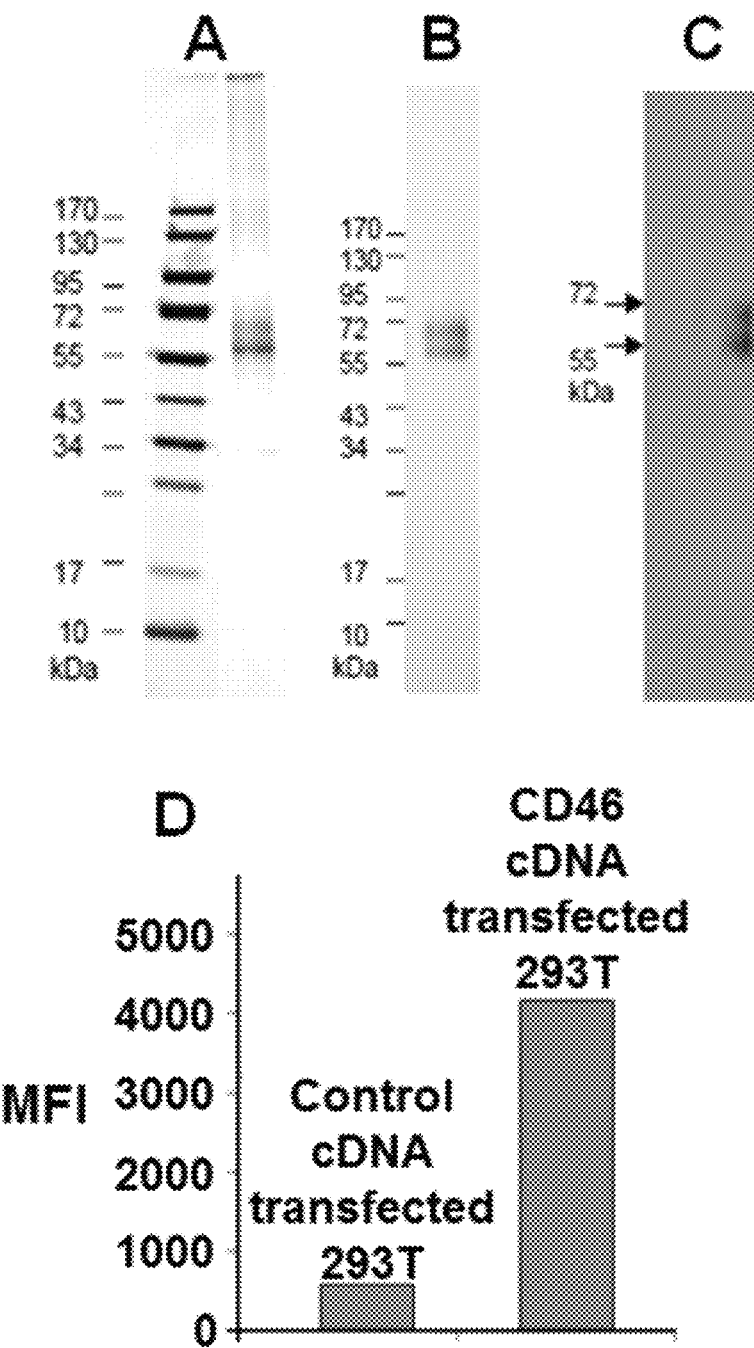
FIG. 1, panels A-D, illustrates the identification of CD46 as the cell surface target of UA20. Panel A: Analysis of immunoprecipitation products by SDS-PAGE and silver staining Cell membrane extracts were prepared and incubated with UA20-conjugated protein A beads. Panel B: Analysis of immunoprecipitates by Western blotting. Tumor cell surface proteins were biotinylated, immunoprecipitated with UA20 and detected by streptavidin-HRP. Referencing the position of the biotin-labeled membrane protein target, corresponding bands on silver stained gel were excised and analyzed by mass spectrometry analysis. Panel C: Confirming antigen identification by Western blotting. Immunoprecipitates from DU145 (antigen positive) and BPH-1 (control, antigen negative) were subjected to Western blotting analysis using anti-CD46 antibodies. Panel D: Confirming antigen identification by ectopic cDNA expression. FACS analysis of UA20 binding to 293T cells transiently transfected with human CD46 cDNA and a control cDNA. Mean fluorescence intensity (MFI) values are indicated.

In various embodiments methods and compositions are provided for the specific delivery of effector moieties (e.g., detectable moieties, cytotoxic and/or cytostatic moieties) to cancer cells (e.g., to prostate cancer cells) are provided. In particular, it was determined that certain prostate tumor targeting internalizing human monoclonal antibodies that bind to prostate tumor cells in situ residing in their tissue microenvironment specifically bind CD46 (e.g., human CD46). The epitope bound by these antibodies was mapped. It was determined that the epitope is conformational and located in the Sushi domain 1 (amino acid sequence: CEEPPTFEAM ELIGKPKPYY EIGERVDYKC KKGY-FYIPPL ATHTICDRNH TWLPVSDDAC YR, SEQ ID NO:19) of CD46.

It was further determined that a 32 amino acid region (KPYYEIGERV DYKCKKGYFY IPPLATHTIC DR, SEQ ID NO:1) in Sushi 1 is necessary for binding. It was found that an anti-CD46 antibody binding to this epitope is preferentially internalized by prostate tumor cells with no significant internalization by normal cells that express CD46. Functional internalization studies using antibody-toxin (saporin) conjugates were performed and it was found that the anti-CD46 antibody-toxin conjugate preferentially kills prostate cancer cells, consistent with the differential internalization that was observed for tumor cells (see, e.g., Example 1).

To further validate the CD46 (Sushi 1) epitope as a therapeutic target, immunohistochemistry studies were performed using a panel of normal and prostate tumor tissues. It was found that this CD46 epitope is expressed by all prostate tumors that were have studied but is not expressed in any significant way by a broad panel of normal human tissues except the placental trophoblasts, which are not present in men, and the normal prostate, which is not a vital organ. Thus this CD46 epitope that we have identified can be targeted by the human monoclonal antibody to allow tumor-selective internalization and targeted tumor killing by the antibody alone or by the use of antibody-toxin or antibody-drug conjugates.

In view of these discoveries, it is believed that antibodies that specifically bind Sushi domain 1 of CD46, and in particular the epitope identified above, will specifically bind and be internalized into cells that express or overexpress CD46. As CD46 is expressed/overexpressed by a number of cancers including, but not limited to ovarian cancer, breast cancer, lung cancer, prostate cancer, colon cancer, kidney cancer, pancreatic cancer mesothelioma, lymphoma, liver cancer, urothelial cancer, stomach cancer, and cervical cancer, these antibodies can be used to specifically target and internalize into these and other CD46 positive cancer cells.

In certain embodiments these anti-Sushi domain 1 antibodies can be used without attached effectors for their intrinsic cytotoxic and/or cytostatic and/or antiproliferative activity on cells (particularly cancer cells). In certain embodiments these antibodies can be attached to one or more effectors (e.g., second antibody, a detectable label, a cytotoxin, a liposome containing a drug, a radionuclide, a drug, a prodrug, a viral particle, a cytokine, and a chelate) to thereby form an immunoconjugate will specifically bind and internalize into cancer cells expressing or overexpressing CD46. In certain embodiments multiple effectors will be attached to a single antibody, or in certain embodiments, multiple antibodies will be attached to a single effector, or in certain embodiments, a single antibody will be attached to a single antibody.

In various embodiments methods of use of these antibodies and/or immunoconjugates are provided. In certain embodiments the methods involve contacting a cell that expresses or overexpresses CD46 (e.g., a cancer cell such as an ovarian cancer cell, a breast cancer cell, a lung cancer cell, a prostate cancer cell, a colon cancer cell, a kidney cancer cell, a pancreatic cancer cell, etc.) with the construct resulting in internalization of the construct (or a portion thereof) into the cell and thereby delivering the effector to the target cell. In certain embodiments the "contacting" comprises administering the antibody or the construct to a subject (e.g., a human or a non-human mammal) in need thereof.

Antibodies that Bind CD46 CCP1

It was discovered that antibodies that specifically bind CD46 Sushi domain 1, and more preferably antibodies that bind the epitope of SEQ ID NO:1, above, effectively bind and are internalized by prostate (and other CD46 positive cancer cells) in situ, e.g., when the cancer cell is in the tissue microenvironment. As indicated above, such antibodies are useful for targeting cancers when used alone, or when attached to an effector to form a "targeted effector".

Accordingly in certain embodiments, an isolated antibody is provided that that specifically binds and is internalized into a prostate cancer cell, where the antibody is an antibody that specifically binds cells that express or overexpress a CD46, where the antibody specifically binds sushi domain 1 of CD46. In certain embodiments the antibody binds an epitope defined by or comprising SEQ ID NO:1.

The antibody designated herein as 2B10 is one such prototypical antibody that was derived from the UA20. A comparison of 2B10 with the UA20 antibody is shown in FIG. 8 and in Table 1. As shown therein, the 2B10 antibody differs from UA20 the amino acid sequences of VH and VL complementarity determining regions (CDR) and in the VH framework 1 region.

TABLE 1

Amino acid sequences of VH and VL chains of
the 2B10 and UA20 antibodies, respectively.

| Antibody | Amino Acid Sequence |
|---|---|

Heavy chain variable region (V$_H$):

|   | Framework 1 | CDR1 | Framework 2 |
|---|---|---|---|
| 2B10VH | QVQLQEPGGGLVQPGRSLRLSCAASGFTFD | DYAMH | WVRQAPGKGLEWVG |
| UA20VH | QVQLQESGGGLVKPGGSLRLSCAASGFTFS | NAWMN | WVRQAPGKGLEWVG |

|   | CDR2 | Framework 3 |
|---|---|---|
| 2B10VH | RIKSKTDEGTTDYAAPVKG | RFSISRDDSKNTLYLQMNSLKTEDTGVYYCTA |
| UA20VH | RIKSKTDEGTTDYAAPVKG | RFSISRDDSKNTLYLQMNSLKTEDTGVYYCTA |

|   | CDR3 | Framework 4 |   |
|---|---|---|---|
| 2B10VH | TKGLGGSK | LGQGTLVTVSS | (SEQ ID NO: 15) |
| UA20VH | TKGLGGSK | LGQGTLVTVSS | (SEQ ID NO: 16) |

Light chain variable region (VL):

|   | Framework 1 | CDR1 | Framework 2 |
|---|---|---|---|
| 2B10VL | QSVLTQPPSASGTPGQRVTISC | SGSSSNIGSNTVS | WSRQLPGTAPKLLI |
| UA20VL | QSVLTQPPSASGTPGQRVTISC | SGSSSNIGNNTVN | WSRQLPGTAPKLLI |

|   | CDR2 | Framework 3 |
|---|---|---|
| 2B10VL | YSNDQRPS | GVPDRFSGSKSGTSASLAITGLQPEDEADYYC |
| UA20VL | YSNDQRPS | GVPDRFSGSKSGTSASLAITGLQPEDEADYYC |

|   | CDR3 | Framework 4 |   |
|---|---|---|---|
| 2B10VL | GTWDSSLSAYV | FGTGTKLTVL | (SEQ ID NO: 17) |
| UA20VL | GTWDSSLSAYV | FGTGTKLTVL | (SEQ ID NO: 18) |

In various embodiments the antibodies contemplated herein expressly exclude antibodies composing the three VH CDRs and/or the three VL CDRs of antibodies 3051.1, G12FC3, M6c42b, 4F3YW, M40pr146, UA20, UAB, 585II41, 585II41.1, 585II56, 3076, 3051, M49R, RCI-14, II79_4, II79_3, T5II-4B.1, T5II-4B.2, RCI-11, RCI-20, CI-11A, CI-14A, S95-2 that are described in PCT/US2008/076704 (WO 2009/039192) and/or the mPA7 antibody. The amino acid sequences of the VH and VL chains of these antibodies and the CDRs comprising these domains are shown in in PCT/US2008/076704 and the amino acid sequences of these domains are reproduced below in Table 2.

TABLE 2

Excluded antibodies. The sequence shown below are scFv antibodies (the VL and VH regions are joined by a (Gly$_4$Ser)$_3$ (SEQ ID NO: 11) linker, however it will be recognized that other antibody forms comprising the CDRs (or the VH and/or VL domains) are similarly excluded.

| Clone | Amino Acid Sequence | SEQ ID No |
|---|---|---|
| 3051.1 | QVQLQESGGGLVKPGGPLRLSCAASGFTFSSYGMYWVRQAPGKG LEWVSTLSRSGSGTYYADSVKGRFTISRDNSKNTLYLQMNSLRA EDTAVYYCASIAVAGNYFDYWGQGTLVTVSSGGGGSGGGGSGGG GSSYVLTQDPAVSVALGQTVRITCQGDSLRSYYASWYQERPGQA PLLVIYGKNNRPSGIPDRFSGSNSGSTATLTISRVEAGDEGYY CQVWDSINEQVVFGGGTKVTVL | 20 |
| G12FC3 | QVQLVQSGGGVVQPGRSLRLSCAATGIPFSGSGMHWVRQAPGKG LEWVTMIWYDGSNKFYADSVKGRFTISRDNSKNTLYLQMDSLRA EDTAVYFCARDKGVRSMDVWGLGTTVTVSSGGGGSGGGGSGGGG SNFMLTQPPSVSVAPGQTAKITCDGYSIRTKSVHWYQQKPGQAP | 21 |

TABLE 2-continued

Excluded antibodies. The sequence shown below are scFv antibodies (the VL and VH regions are joined by a (Gly$_4$Ser)$_3$ (SEQ ID NO: 11) linker, however it will be recognized that other antibody forms comprising the CDRs (or the VH and/or VL domains) are similarly excluded.

| Clone | Amino Acid Sequence | SEQ ID No |
|---|---|---|
| | VVVVHDDSDRPSGIPERFSGSNSGTTATLTISRVEAGDEADYYC QAWDSISEEVVFGGGTKLTVL | |
| M6c42b | QVQLQESGGGLVQPGGSLRLSCSASGFTFGTYAMRWVRQTSGKG LEWVSGIGVSGDAYYTDSVRGRFTISRDNSKNTLYLQMNTLRAE DTATYYCTRKSSTTSNDYWGRGTLVTVSSGGGGSGGGGSGGGGS SYVLTQDPAVSVALGQTVRITCQGDNIGSKSVHWYQQKPGQAPV LVVYDDSDRPSGIPERFSGSNSGTTATLTISSVEAGDEADYYCQ AWDSISEHVIFGGGTKVTVL | 22 |
| 4F3YW | QVQLQESGGGLVQPGGSLRLSCAASGFTFSSYAMHWVRQAPGKG LEWVAVISYDGSNKYYADSVKGRFTISRDNSKNTLYLQMNSLRA EDTAVYYCARFSSGWYYFDYWGQGTLVTVSSGGGGSGGGGSGGG GSDIQMTQSPSFLSASVGDRITITCRASHDISSYFAWYQQKPGK APKPLIYAASTLQSGVPSRFSGSGSGTEFTLTISSLQPEDFATY YCQQLGSYPLTFGGGTKLEIK | 23 |
| M40pr146 | QVQLLQSGGGLVQPGGSLRLSCAASGFTFSSYAMSWVRQAPGKG LEWVSAISGSGGSTYYTDSVKGRFTISRDNSKNTLYLQMNSLRA EDTAVYYCAKSHDYGDYAGFDYWGQGTLVTVSSGGGGSGGGGSG GGGSHVILTQDPAVSVALGQTVRITCQGDSLKSYYASWYQQKPG QAPVLVIYGKNNRPSGIPDRFSGSSSGTTASLTITGAQAEDEAD YYCHSRDSSGTHLRVFGGGTKLTVL | 24 |
| UA20 | QVQLQESGGGLVKPGGSLRLSCAASGFTFSNAWMNWVRQAPGKG LEWVGRIKSKTDEGTTDYAAPVKGRFSISRDDSKNTLYLQMNSL KTEDTGVYYCTATKGLGGSKLGQGTLVTVSSGGGGSGGGGSGGG GSQSVLTQPPSASGTPGQRVTISCSGSSSNIGNNTVNWSRQLPG TAPKLLIYSNDQRPSGVPDRFSGSKSGTSASLAITGLQPEDEAD YYCGTWDSSLSAYVFGTGTKLTVL | 25 |
| UA8 | QVQLVESGGGVVQPGRSLRLSCAASGFTFSSFGMHWVRRAPGKG LEWVAVISYDGSNQYYADSVKGRFTISRDNSKNTLYLQMNSLRA EDTAVYYCGSRPGGYASGSTVAYWGQGTPVTVSSGGGGSGGGG SGGGGSSSELTQDPAVSVALGQTVRITCQGDSLRSYYASWYQQK PGQAPLLVIYGQNIRPSGIPDRFSGSSSGNSASLTITGAQAEDE ADYYCHSRDSSGKYVFGVGTKVTVL | 26 |
| 585I41 | QVQLVESGGGLVQPGGSLRLSCAASGFTFSSYAMGWVRQAPGKG LEWVSAISGSGGSTYYADSVKGRFTISRDNSKDTLYLQMNSLRA EDTAVYYCASRSLLDYWGQGTLVTVSSGGGGSGGGGSGGGGSNF MLTQDPAVSVALGQTVRITCQGDSLRSYYASWYQQKPGQAPLLV IYGKNNRPSGIPDRFSGSSSGNTASLTITGAQAEDEADYYCNSR DSSGNPVFGGGTKVTVL | 27 |
| 585I41.1 | QVQLVESGGGLVQPGGSLRLSCAASGFTFSSYAMSWVRQAPGKG LEWVSAISGSGGSTYYADSVKGRFTISRDNSKDTLYLQMNSLRA EDTAVYYCASRSLLDYWGQGTLVTVSSGGGGSGGGGSGGGGSNF MLTQDPAVSVALGQTVRITCQGDSLRSYYASWYQQKPGQAPLLV IYGKNNRPSGIPDRFSGSSSGNTASLTITGAQAEDEADYYCNSR DSSGNPVFGGGTKVTVL | 28 |
| 585I56 | QVQLQESGGGLVQLGGSLRLSCAASGFTFSSYAMSWVRQAPGKG LEWVSAISGSGGSTYYADSVKGRFTISRDNSKNTLYLQMSSLRA EDTAFYYCANSAYTGGWYDYWGHGTLVTVSSGGGGSGGGGSGGG GSSSELTQDPAVSVALGQTVKITCQGDSLRTYYASWYQQRPGQA PVLVIYGENSRPSGIPDRFSGSSSGNTASLTITGAQAEDEADYY CNSRDSSGNHLRVFGGGTKLTVL | 29 |
| 3076 | QVNLRESGGGLVQPGGFLRLSCAAFGFTFSGYWMSWVHPAPGKG LEWVANIKQDGSEKFYVDSVKGRFTISRDNAKNSLFLQMNSLRA EDTAVYFCARGLLSDYWGQGTLVPVSSGGGGSGGGGSGGGGSNF MLTQPPSVSVAPGKTASLTCGGYNIGTKSVHWYQQKPGQAPVVV VHDDSDRPSGIPERFSGSNSGTTATLTIIRVEAGDEADYYCQAW DSISEEVVFGGGTKLTVL | 30 |
| 3051 | QVQLQESGGGLVKPGGPLRLSCAASGFTFSSYGMYWVRQAPGKG LEWVSTLSRSGSGTYYAESVKGRFTISRDNSKNTLYFQMNSLRA EDTAVYYCASIAVAGNYFEYWGQGTLVTVSSGGGGSGGGGSGGG GSSYVLTQDPAVSVALGQTVRITCQGDSLRSYYASWYQERPGQA | 31 |

TABLE 2-continued

Excluded antibodies. The sequence shown below are scFv antibodies (the VL and VH regions are joined by a (Gly₄Ser)₃ (SEQ ID NO: 11) linker, however it will be recognized that other antibody forms comprising the CDRs (or the VH and/or VL domains) are similarly excluded.

| Clone | Amino Acid Sequence | SEQ ID No |
|---|---|---|
| | PLLVIYGKNNRPSGIPDRFSGSNSGSTATLTISRVEAGDEGDYY CQVWDSINEQVVFGGGTKVTVL | |
| M49R | QVQLQESGGGLVKPGESLRLSCAASGFTFSDHYMDWVRQAPGKG LEWVAYIRYDGSTKYYADSVKGRFTISRDNSKNTLYLQMNSLRP EDTAFYYCARLIAEAEGWFDPWGQGTLVTVSSGGGGSGGGGSGG GGSNFMLTQPPSVSVAPGKTARITCGGNNIGSKSVYWYQQKPGQ APVLVVYDDSDRPSGIPERFSGSNSGNTATLTISRVEAGDEADY YCQVWDSSSDHVVFGGGTKVTVL | 32 |
| RCI-14 | QVQLLQSAGGLVQPGGSLRLSCAASGFTFSTYAMNWVRQAPGKG LEWVSGISGSGGSTNYADSVKGRFTISRDSSKNTLFLQMNSLRA EDTAVYYCAKDYGSGWYDYWGQGTLVTVSSGGGGSGGGGSGGGG SSSELTQDPAVSVALGQTVRITCQGDSLRSYYASWYQERPGQAP LLVIYGRNERPSGIPDRFSASSSGNTASLTITGAQAEDEADYYC QVWDSFNEQVVFGGGTKLTVL | 33 |
| II79_4 | QVQLVESGGGLVQPGGSLRLSCAASGFTFSSYAMSWVHQAPGKG LEWVSAISGSGGSTYYADSVKGRFTISRDNSKNTLYLQMNSLRA EDTAVYYCAKTYYGFWSGYYDYLGQGTLVTVSSGGGGSGGGGSG GGGSSSELTQDPAVSVGLGQTVTITCQGDSLRSYYANWYQQKPG QAPILVIYGENNRPSGIPDRFSGSSSGNTASLTITGAQAEDEAD YYCHSRDSSGTHLRVFGGGTKLTVL | 34 |
| II79_3 | QVQLLESGGGVVQPGTSLRLSCAASGFTFSNYAINWVRQAAGKG LEWVSGISGSGVSTSYADSVKGRFTVSRDNSKNTLYLQMNSLRV EDTALYYCAKNGGGPEYLQHWGQGTLVTVSSGGGGSGGGGSGGG GSQSVLTQPPSASGTPGQRVTISCSGSSSNIGNNTVNWSRQLPG TAPKLLIYSNDQRPSGVPDRFSGSKSGTSASLAITGLQPEDEAD YYCGTWDSSLSAYVFGTGTKLTVL | 35 |
| T5II-4B.1 | QVQLQESGGTLVQPGGSLRLSCAASGFTFSSYAMSWVRQAPGRG LEWVSTISGSGGSTYYADSVKGRFTISRDNSKNTLYLQMNSLRA EDTAVYYCAKGAYSGSYWGQGTLVTVSSGGGGSGGGGSGGGGSS SELTQDPAVSVALGQTVRITCQGDSLRSYYASWYQQKPGQAPSL VIYGENSRPSGIPDRFSGSSSGNTASLTITGAQAENEADYYCQA WDSSTAVVFGGGTKLTVL | 36 |
| T5II-4B.2 | QVQLQESGGTLVQPGGSLRLSCAASGFTFSSYAMSWVRQAPGRG LEWVSTISGSGGSTYYADSVKGRFTISRDNSKNTLYLQMNSLRA EDTAVYYCAKGAYSGSHWGQGTLVTVSSGGGGSGGGGSGGGGSS SELTQDPAVSVALGQTVRITCQGDSLRSYYASWYQQKPGQAPSL VIYGENSRPSGIPDRFSGSSSGNTASLTITGAQAENEADYYCQA WDSSTAVVFGGGTKLTVL | 37 |
| RCI-11 | QVQLVESGAEVKKPGASVKVSCKASGYTFTSYGISWVRQAPGQG LEWMGWISAYNGNTNYAQKLQGRVTMTTDTSTSTAYMELRSLRS DDTAVYYCARPIYDSSGYDAFDIWGQGTMVTVSSGGGGSGGGGS GGGGSDIVMTQSPSTLSASIGDRVTITCRASEGIYHWLAWYQQK PGKAPKLLIYKASSLASGAPSRFSGSGSGTDFTLTISSLQPDDF ATYYCQQYHTISRTFGPGTKVDIK | 38 |
| RCI-20 | QVQLVESGGGLVKPGGSLRLSCAASGFTFSSYAMHWVRQAPGKG LEWVAVISYDGSNKYYADSVKGRFTISRDNSKNTLYLQMNSLRA EDTAVYFCVRPSDSGWSFEHWGQGTLVPVSSGGGGSGGGGSGGG GSQSVLTQPPSASGTPGQRVTISCSGSSSNIGNNTVNWSRQLPG TAPKLLIYSNDQRPSGVPDRFSGSKSGTSASLAITGLQPEDEAD YYCGTWDSSLSAYVFGTGTKLTVL | 39 |
| CI-11A | <u>QVQLQESGGGLVQPGGSLRLSCAASGFTFSSYAMSWVRQAPGKG LEWVAVISYDGSNKYYADSVKGRFTISRDNSKNTLYLQMNSLRA EDTAVYYCVRGDRSYGAEYFQHWGQGTLVTVSS</u>GGGGSGGGGSG GGGSSSELTQDPAVSASGQTVRITCQGDSLRSYYASWYQQKPG QAPLLVIYGKNIRPSGIPDRFSGSTSGNSASLTITGAQAEDEAD YYCNSRDSSGNRNWVFGGGTKLTVL | 40 |
| CI-14A | <u>QVQLQESGGGLVKPGGSLRLSCAASGFTSSSYAMHWVRQAPGKG LEYVSAIGGNGGTYYADSVKGRFTISRDNSKNTLYLQMNSLRAE DTAVYYCAKEGEQWLEYRYYYGMDVWGQGTTVTVSS</u>GGGGSGGG GSGGGGSSSELTQDPAVSVALGQTVRITCQGDSLRSYYASWYQQ | 41 |

TABLE 2-continued

Excluded antibodies. The sequence shown below are scFv antibodies (the VL and VH regions are joined by a (Gly$_4$Ser)$_3$ (SEQ ID NO: 11) linker, however it will be recognized that other antibody forms comprising the CDRs (or the VH and/or VL domains) are similarly excluded.

| Clone | Amino Acid Sequence | SEQ ID No |
|---|---|---|
| | KPGQAPSLVIYGENSRPSGIPDRFSGSSSGNTASLTITGAQAEN EADYYCQAWDSSTAVVFGGGTKLTVL | |
| S95-2 | QVQLVESGGGVVQPGRSLRLSCTASGFTFSSYGMHWVRQAPGKG LEWVAVISYDGSNKYYADSVKGRFTISRDNSKNTLYLQMNSLRA EDTAVYYCARGGRYSSNWFSYYYYGMDVWGQGTTVTVSSGGGGS GGGGSGGGGSNFMLTQPPSVSVAPGKTARITCGGNNIGSKSVYW YQQKPGQAPVLVVYDDSDRPSGIPERFSGSNSGNTATLTISRVE AGDEADYYCQVWDSSSDHVVFGGGTKVTVL | 42 |

Using the amino acid sequence provided for the 2B10 antibody, numerous antibody forms can be prepared, e.g., as described below. Such forms include, but are not limited to a substantially intact (e.g., full length) immunoglobulin (e.g., an IgA, IgE, IgG, and the like), an antibody fragment (e.g., Fv, Fab, (Fab')$_2$, (Fab')$_3$, IgGΔCH$_2$, a minibody, and the like), a single chain antibody (e.g., scFv), a diabody, a unibody, an affibody, and the like.

It will be recognized, that where the antibodies are single chain antibodies, the VH and VL domains comprising such antibody can be joined directly together or by a peptide linker. Illustrative peptide linkers include, but are not limited to GGGGS GGGGS GGGGS (SEQ ID NO:2), GGGGS GGGGS (SEQ ID NO:3), GGGGS (SEQ ID NO:4), GS GGGGS GGGGS GGS GGGGS (SEQ ID NO:5), SGGGGS (SEQ ID NO:6), GGGS (SEQ ID NO:7), VPGV (SEQ ID NO:8), VPGVG (SEQ ID NO:9), GVPGVG (SEQ ID NO:10), GVG VP GVG (SEQ ID NO:11), VP GVG VP GVG (SEQ ID NO:12), GGSSRSS (SEQ ID NO:13), and GGSSRSSSSGGGGSGGGG (SEQ ID NO:14), and the like.

As indicated above, in various embodiments, the antibody binds (e.g., specifically binds CD46 sushi domain 1 (CCP1), and more preferably binds to an epitope consisting of or comprising the amino acid sequence of SEQ ID NO:1. Typically antibodies contemplated herein will specifically bind prostate cancer cells including, but not limited to cells of a cell line selected from the group consisting of DU145 cells, PC3 cells, and LnCaP cells. In certain embodiments the antibody binds to a prostate tumor cell with an affinity greater than ($K_D$ less than) about 5 nM when measured on live prostate tumor cells by FACS. In certain embodiments the affinity is greater than (KD less than) about 1 nM, or at about 100 pM, or about 50 pM, or about 10 pM, or about 1 pM.

Using the sequence information provided herein antibodies comprising one or more of the CDRs comprising, e.g., 2B10, or antibodies comprising the VH and/or VL domain(s) of these antibodies can readily be prepared using standard methods (e.g. chemical synthesis methods and/or recombinant expression methods) well known to those of skill in the art, e.g., as described below.

In addition, other "related" prostate cancer specific antibodies can be identified by screening for antibodies that bind to the same epitope (e.g., CD46 sushi domain 1 and/or an epitope comprising the amino acid sequence of SEQ ID NO:1 (e.g. that compete with the 2B10 antibody for binding to a prostate cancer cell) and/or by modification of the 2B10 antibody identified herein to produce libraries of modified antibody and then rescreening antibodies in the library for improved binding to prostate cancer cells, specifically to CD46 sushi domain 1.

Identification of Other Antibodies Binding the Same CD46 CCP1 Epitope(s) as 2B10.

Having identified CD46 CCP1, preferably the epitope of SEQ ID NO:1 as a useful antibody target and 2B10 antibody as a useful prototypical antibody, other "related" antibodies that bind CD46 CCP1, preferably binding the epitope of SEQ ID NO:1 can readily be identified by screening for antibodies that bind CD46 CCP1 (especially SEQ ID NO:1), e.g., by raising (e.g., monoclonal antibodies) that specifically bind CD46 CCP1 (especially SEQ ID NO:1). Additionally or alternatively, other antibodies that bind CD46 CCP1 (especially SEQ ID NO:1), can be identified by screening for antibodies that that cross-react with the 2B10 antibody, e.g., at the epitope bound by 2B10, and/or for antibodies that cross-react with the 2B10 antibody for binding to a prostate cancer cell (e.g., CaP cells, PC3 cells, etc.), and/or with an idiotypic antibody raised against the 2B10 antibody.

Monoclonal Antibodies.

Monoclonal antibodies that bind CD46 CCP1, preferably binding the epitope of SEQ ID NO:1 can be produced using a variety of known techniques, such as the standard somatic cell hybridization technique described by Kohler and Milstein (1975) Nature 256: 495, viral or oncogenic transformation of B lymphocytes or phage display technique using libraries of human antibody genes. In particular embodiments, the antibodies are fully human monoclonal antibodies.

Accordingly, in one embodiment, a hybridoma method is used for producing an antibody that binds CD46 CCP1, preferably binding the epitope of SEQ ID NO:1. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding (1986) Monoclonal Antibodies: Principles and Practice, pp. 59-103 (Academic Press)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Id.). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies and antibody portions that bind CD46 CCP1, preferably binding the epitope of SEQ ID NO:61 can be isolated from antibody phage libraries generated using the techniques described in, for example, McCafferty et al. (1990) Nature, 348: 552-554, Clackson et al. (1991) Nature, 352:624-628, Marks et al. (1991) J. Mol. Biol., 222: 581-597, Hoet et al (2005) Nature Biotechnol., 23: 344-348; U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al. (1992) Bio/Technology, 10:779-783), as well as combinatorial infection and in vivo recombination as a strategy for constructing very large phage libraries (Waterhouse et al. (1993), Nuc. Acids. Res., 21: 2265-2266) may also be used.

In a particular embodiment, the monoclonal antibody or antigen binding portion thereof that binds CD46 CCP1, preferably binding the epitope of SEQ ID NO:1 is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to CD46 CCP1, preferably comprising the epitope of SEQ ID NO:1.

In yet another embodiment, human monoclonal antibodies directed against CD46 CCP1, preferably comprising the epitope of SEQ ID NO:1 can be generated using transgenic or transchromosomic mice carrying parts of the human immune system rather than the mouse system (see e.g., Lonberg, et al. (1994) Nature 368(6474): 856-859; Lonberg and Huszar, (1995) Intern. Rev. Immunol. 13: 65-93, Harding and Lonberg (1995) Ann. NY. Acad. Sci. 764: 536-546, and U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

In another embodiment, human antibodies directed against CD46 CCP1, preferably binding the epitope of SEQ ID NO:1 can be raised using a mouse that carries human immunoglobulin sequences on transgenes and transchomosomes, such as a mouse that carries a human heavy chain transgene and a human light chain transchromosome (see e.g., PCT Publication WO 02/43478 to Ishida et al.).

Alternative transgenic animal systems expressing human immunoglobulin genes are available in the art and can be used to raise anti-CD46 CCP antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Alternative transchromosomic animal systems expressing human immunoglobulin genes are available in the art and can be used to raise anti-CD46 CCP1 antibodies contemplated herein. For example, mice carrying both a human heavy chain transchromosome and a human light chain tranchromosome can be used; as described in Tomizuka et al. (2000) Proc. Natl. Acad. Sci. USA 97: 722-727. Furthermore, cows carrying human heavy and light chain transchromosomes have been described in the art (see, e.g., Kuroiwa et al. (2002) *Nature Biotechnology* 20: 889-894) and can be used to raise anti-CD46 CCP1 antibodies.

In yet another embodiment, antibodies that specifically bind CD46 CCP1, preferably binding the epitope of SEQ ID NO:1 can be prepared using a transgenic plant and/or cultured plant cells (such as, for example, tobacco, maize and duckweed) that produce such antibodies. For example, transgenic tobacco leaves expressing antibodies or antigen binding portions thereof can be used to produce such antibodies by, for example, using an inducible promoter (see, e.g., Cramer et al. (1999) *Curr. Top. Microbol. Immunol.* 240: 95-118). Also, transgenic maize can be used to express such antibodies and antigen binding portions thereof (see, e.g., Hood et al. (1999) *Adv. Exp. Med. Biol.* 464: 127-147). Antibodies can also be produced in large amounts from transgenic plant seeds including antibody portions, such as single chain antibodies (scFv's), for example, using tobacco seeds and potato tubers (see, e.g., Conrad et al. (1998) *Plant Mol. Biol.* 38: 101-109). Methods of producing antibodies or antigen binding portions in plants can also be found in, e.g., Fischer et al. (1999) *Biotechnol. Appl. Biochem.* 30: 99-108, Ma et al. (1995) *Trends Biotechnol.* 13: 522-527, Ma et al. (1995) *Plant Physiol.* 109: 341-346; Whitelam et al. (1994) *Biochem. Soc. Trans.* 22: 940-944, and U.S. Pat. Nos. 6,040,498 and 6,815,184.

The binding specificity of monoclonal antibodies or portions thereof that bind CD46 CCP1, preferably comprising the epitope of SEQ ID NO:61 prepared using any technique including those disclosed here, can be determined by immunoprecipitation or by an in vitro binding assay, such as radioimmunoassay (RIA) or enzyme-linked immunoabsorbent assay (ELISA). The binding affinity of a monoclonal antibody or portion thereof also can be determined by the Scatchard analysis of Munson et al. (1980) *Anal. Biochem.*, 107:220.

Cross-Reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein (e.g., 2B10) using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine) In general, it is desirable to use a myeloma cell line which does not secrete an immunoglobulin. Several such lines are known in the art. One generally preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology*, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

Cross-Reactivity with the 2B10 Antibody.

In another approach, antibodies that bind CD46 CCP1, preferably the epitope of SEQ ID NO:1 can be identified by the fact that they bind the same epitope as the "prototypic" antibodies of this invention (e.g., 2B10)). To identify such antibodies, it s not necessary to isolate the subject epitope. In certain embodiments, one can screen, e.g. antibody libraries for antibodies that compete with the prototypic antibodies of this invention for binding and/or internalization by a prostate cancer cell (e.g. a CaP cell, a PC3 cell, etc.), and/or for binding to the CD46 CCP1 epitope identified herein.

Methods of screening libraries for epitope binding and/or cell binding and/or internalization are well known to those of skill in the art. In certain embodiments, cross-reactive prostate antibodies show at least 60%, preferably 80%, more preferably 90%, and most preferably at least 95% or at least 99% cross-reactivity with the 2B10 antibody described herein.

Phage Display Methods to Select Other "Related" Anti-CD46 CCP1 Antibodies.

Using the known sequences for the 2B10 antibody and/or other prostate specific antibodies, a variety of phage display (or yeast display) methods can be used to generate other antibodies that antibodies that specifically bind CD46 CCP1, preferably binding the epitope of SEQ ID NO:1, with the same or even greater affinity.

Chain Shuffling Methods.

One approach to creating creating antibody variants has been to replace the original $V_H$ or $V_L$ gene with a repertoire of V-genes to create new partners (chain shuffling) (Clackson et al. (1991) *Nature*. 352: 624-628) in a phage display or yeast display library. Using chain shuffling and phage display, the affinity of a human scFv antibody fragment that bound the hapten phenyloxazolone (phOx) was increased from 300 nM to 1 nM (300 fold) (Marks et al. (1992) *Bio/Technology* 10: 779-783).

Thus, for example, to alter the affinity of an anti-CD46 CCP1 antibody, a mutant scFv gene repertoire can be created containing a $V_H$ gene of the prototypic 2B10 antibody (e.g. as shown in Table 1) and a human $V_L$ gene repertoire (light chain shuffling). The scFv gene repertoire can be cloned into a phage display vector, e.g., pHEN-1 (Hoogenboom et al. (1991) *Nucleic Acids Res.*, 19: 4133-4137) or other vectors, and after transformation a library of transformants is obtained.

Similarly, for heavy chain shuffling, a mutant scFv gene repertoire can be created containing a $V_L$ gene of the prototypic 2B10 antibody (e.g. as shown in Table 1) and a human $V_H$ gene repertoire (heavy chain shuffling). The scFv gene repertoire can be cloned into a phage display vector, e.g., pHEN-1 (Hoogenboom et al. (1991) *Nucleic Acids Res.*, 19: 4133-4137) or other vectors, and after transformation a library of transformants is obtained.

The resulting libraries can be screened against the relevant target (e.g., CD46 CCP1 antibody) and/or for cross-reactivity with 2B10.

Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.*, 196: 901-917; Chothia et al. (1986) *Science*, 233: 755-8; Nhan et al. (1991) *J. Mol. Biol.*, 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.*, 234: 564-578; Wells (1990) *Biochemistry*, 29: 8509-8516). Site-directed mutagenesis of CDRs and screening against the prostate cancer cells, in particular for binding at CD46 CCP1 e.g. as described herein in the examples, can produce antibodies having improved binding affinity.

CDR Randomization to Produce Higher Affinity Human scFv.

In an extension of simple site-directed mutagenesis, mutant antibody libraries can be created where partial or entire CDRs are randomized ($V_L$ CDR1 CDR2 and/or CDR3 and/or $V_H$ CDR1, CDR2 and/or CDR3). In one embodiment, each CDR is randomized in a separate library, using a known antibody (e.g., 2B10) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.*, 234: 564-578).

$V_H$ CDR3 often occupies the center of the binding pocket, and thus mutations in this region are likely to result in an increase in affinity (Clackson et al. (1995) *Science*, 267: 383-386). In one embodiment, four $V_H$ CDR3 residues are randomized at a time using the nucleotides NNS (see, e.g., Schier et al. (1996) *Gene*, 169: 147-155; Schier and Marks (1996) *Human Antibodies and Hybridomas*. 7: 97-105, 1996; and Schier et al. (1996) *J. Mol. Biol.* 263: 551-567).

Other Antibody Modifications.

In one embodiment, partial antibody sequences derived from the 2B10 antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332: 323-327; Jones et al., (1986) *Nature* 321: 522-525; and Queen et al. (1989) *Proc. Natl. Acad. Sci. USA*, 86: 10029-10033). Such framework sequences can be obtained from public DNA databases that include germline antibody gene sequences.

Thus, one or more structural features of an anti-CD46 CPP1 antibody of the invention, such as the CDRs, can be used to create structurally related anti-CD46 CPP1 antibodies that retain at least one functional property of, for example, the 2B10 antibody, e.g., binding and internalizing into prostate cancer cells.

In a particular embodiment, one or more 2B10 CDR regions (e.g. VH CDR1, and/or CDR2, and/or CDR3, and/or VL CDR1, and/or CDR2, and/or CDR3) is combined recombinantly with known human framework regions and CDRs to create additional, recombinantly-engineered, anti-CD46 CPP1 antibodies. The heavy and light chain variable framework regions can be derived from the same or different antibody sequences.

It is well known in the art that antibody heavy and light chain CDR3 domains play a particularly important role in the binding specificity/affinity of an antibody for an antigen (see, e.g., Hall et al. (1992) *J. Immunol.*, 149: 1605-1612; Polymenis et al. (1994) *J. Immunol.*, 152: 5318-5329; Jahn et al. (1995) *Immunobiol.*, 193:400-419; Klimka et al. (2000) *Brit. J. Cancer*, 83: 252-260; Beiboer et al. (2000) *J. Mol. Biol*, 296: 833-849; Rader et al. (1998) *Proc. Natl. Acad. Sci. USA*, 95: 8910-8915; Barbas et al. (1994) *J. Am. Chem. Soc.*, 116: 2161-2162; Ditzel et al. (1996) *J. Immunol.*, 157: 739-749). Accordingly, in certain embodiments, antibodies are generated that include the heavy and/or light chain CDR3s of the particular antibodies described herein (e.g., 2B10). It is also noted, however that 2B10 differs from UA20 antibody, in part, by mutations in CDR1. Accordingly, in certain embodiments, antibodies are generated that include the heavy and/or light chain CDR1s of the particular antibodies described herein (e.g., 2B10). The antibodies can further include the other heavy and/or light chain CDRs of the antibodies of the present invention (e.g., 2B10).

In certain embodiments the CDR1, 2, and/or 3 regions of the engineered antibodies described above can comprise the exact amino acid sequence(s) as those disclosed herein (e.g., CDRs of 2B10). However, the ordinarily skilled artisan will appreciate that some deviation from the exact CDR sequences may be possible while still retaining the ability of the antibody to bind CD46 CPP1 effectively (e.g., conservative amino acid substitutions). Accordingly, in another embodiment, the engineered antibody may be composed of one or more CDRs that are, for example, 90%, 95%, 98%, 99% or 99.5% identical to one or more CDRs of the 2B10 antibody.

In another embodiment, one or more residues of a CDR may be altered to modify binding to achieve a more favored on-rate of binding. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC) (see, e.g., Caron et al. (1992) *J. Exp Med.* 176: 1191-1195; Shopes (1992) *J. Immunol.* 148: 2918-2922). Homodimeric antibodies with enhanced anti-tumor activity may also be prepared using heterobifunctional cross-linkers (see, e.g., Wolff et al. (1993) *Cancer Res.* 53:2560-2565). Alternatively, an antibody can be engineered which has dual Fc regions and may thereby have enhanced complement lysis and ADCC capabilities (see, e.g., Stevenson et al. (1989) *Anti-Cancer Drug Design* 3: 219-230).

Antibody Production.

In various embodiments antibodies described herein can be produced by chemical synthesis or can be recombinantly expressed.

Chemical Synthesis.

Using the sequence information provided herein, the CD46 Sushi domain 1 specific antibodies described herein (e.g., 2B10), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis*; pp. 3-284 in *The Peptides: Analysis, Synthesis, Biology*. Vol. 2: *Special Methods in Peptide Synthesis*, Part A., Merrifield et al. (1963) *J. Am. Chem. Soc.*, 85: 2149-2156, and Stewart et al. (1984) *Solid Phase Peptide Synthesis,* 2nd ed. Pierce Chem. Co., Rockford, Ill.

Recombinant Expression of Prostate Cancer-Specific Antibodies.

In certain embodiments, the CD46 Sushi domain 1 specific antibodies described herein (e.g., 2B10), or variants thereof, are recombinantly expressed using methods well known to those of skill in the art. For example, using the 2B10 sequence information provided herein, nucleic acids encoding the desired antibody can be prepared according to a number of standard methods known to those of skill in the art. The nucleic acids are transfected into host cells that then express the desired antibody or a chain thereof.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl. Acad. Sci. USA* 86: 10029-10033. In addition, detailed protocols for the expression of antibodies are also provided by Liu et al. (2004) *Cancer Res.* 64: 704-710, Poul et al. (2000) *J. Mol. Biol.* 301: 1149-1161, and the like.

Creation of Other Antibody Forms.

Using the known and/or identified sequences (e.g. $V_H$ and/or $V_L$ sequences) of the single chain antibodies provided herein other antibody forms can readily be created. Such forms include, but are not limited to multivalent antibodies, full antibodies, scFv, (scFv')$_2$, Fab, (Fab')$_2$, chimeric antibodies, and the like.

Creation of Homodimers.

For example, to create (scFv')$_2$ antibodies, two anti-CD46 CPP1 antibodies are joined, either through a linker (e.g., a carbon linker, a peptide, etc.) or through a disulfide bond between, for example, two cysteins. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM 3-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimmer can be determined using standard methods, e.g. by BIAcore.

In one illustrative embodiment, the (scFv')$_2$ dimer is created by joining the scFv' fragments through a linker, e.g., through a peptide linker. This can be accomplished by a wide variety of means well known to those of skill in the art. For example, one approach is described by Holliger et al. (1993) *Proc. Natl. Acad. Sci. USA,* 90: 6444-6448 (see also WO 94/13804).

It is noted that using the $V_H$ and/or $V_L$ sequences provided herein Fabs and (Fab')$_2$ dimers can also readily be prepared. Fab is a light chain joined to $V_H$-$C_H$1 by a disulfide bond and can readily be created using standard methods known to those of skill in the art. The F(ab)'$_2$ can be produced by dimerizing the Fab, e.g. as described above for the (scFv')$_2$ dimer.

Chimeric Antibodies.

The antibodies contemplated herein also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein (e.g., 2B10) are fully human antibodies, chimeric antibodies are contemplated, particularly when such antibodies are to be used in species other than humans (e.g., in veterinary applications). Chimeric antibodies are antibodies comprising portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643) and anti-tumor antigens (see, e.g., Sahagan et al. (1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line that produces an anti-CD46 CPP1 (e.g., a prostate cancer specific) antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of a prostate cancer specific antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

3) Intact Human Antibodies.

In another embodiment, this invention provides for intact, fully human anti-CD46 CPP1 (e.g., prostate cancer specific) antibodies. Such antibodies can readily be produced in a manner analogous to making chimeric human antibodies. In this instance, instead of using a recognition function derived, e.g. from a murine, the fully human recognition function (e.g., VH and $V_L$) of the antibodies described herein is utilized.

4) Diabodies.

In certain embodiments, diabodies comprising one or more of the $V_H$ and $V_L$ domains described herein are contemplated. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444-6448.

5) Unibodies.

In certain embodiments using the sequence information provided herein, the anti-CD46 CPP1 antibodies can be constructed as unibodies. UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule leaves only one area on the UniBody that can bind to a target. Methods of producing unibodies are described in detail in PCT Publication WO2007/059782, which is incorporated herein by reference in its entirety (see, also, Kolfschoten et al. (2007) *Science* 317: 1554-1557).

6) Affibodies.

In certain embodiments the sequence information provided herein is used to construct affibody molecules that CD46 CPP1. Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.*, 269: 2647-2655.). Details of Affibodies and methods of production are known to those of skill (see, e.g., U.S. Pat. No. 5,831,012 which is incorporated herein by reference in its entirety).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the antibody and/or immunoconjugate is to be used. In other words, for use in a human, it is desirable to use a human, humanized, or chimeric human antibody.

Measurement of Antibody/Polypeptide Binding Affinity.

As explained above, selection for increased avidity can involves measuring the affinity of the antibody for the target antigen (e.g., CD46 CPP1, especially the epitope comprising or consisting of SEQ ID NO:1). Methods of making such measurements are well known to those of skill in the art. Briefly, for example, the $K_d$ of the antibody is determined from the kinetics of binding to, e.g. the target cell in a BIAcore, a biosensor based on surface plasmon resonance. For this technique, the antigen or cell is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

Immunoconjugates Comprising 2B10 or Other Anti-CD46 CCP1 (e.g., Anti-SEQ ID NO:6) Antibodies.

The prototypical anti-CD46 CCP1 antibody (2B10) described herein specifically binds to and is internalized by prostate cancer cells and by other CD46 positive cancer cells. The antibodies can be used alone as therapeutics (e.g., to inhibit growth and/or proliferation of a prostate cancer cell) or they can be coupled to an effector forming immunoconjugates that provide efficient and specific delivery of the effector (e.g. cytotoxins, labels, radionuclides, ligands, antibodies, drugs, liposomes, nanoparticles, viral particles, cytokines, and the like) to various cancer cells that express CD46 (e.g., isolated cells, metastatic cells, solid tumor cells, etc.).

Anti-CD46 CPP1 immunoconjugates can be formed by conjugating the antibodies or antigen binding portions thereof described herein to an effector (e.g., a detectable label, another therapeutic agent, etc.). Suitable agents include, for example, a cytotoxic or cytostatic agent (e.g., a chemotherapeutic agent), a toxin (e.g. an enzymatically active toxin of bacterial, fungal, plant or animal origin, or fragments thereof), and/or a radioactive isotope (i.e., a radioconjugate).

In certain embodiments, the effector comprises a detectable label. Suitable detectable labels include, but are not limited to radio-opaque labels, nanoparticles, PET labels, MRI labels, radioactive labels, and the like. Among the radionuclides and useful in various embodiments of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing prostate cancer cells. Such detection/visualization can be useful in various contexts including, but not limited to pre-operative and intraoperative settings. Thus, in certain embodiment this invention relates to a method of intraoperatively detecting and prostate cancers in the body of a mammal. These methods typically involve administering to the mammal a composition comprising, in a quantity sufficient for detection by a detector (e.g. a gamma detecting probe), an prostate cancer specific antibody labeled with a detectable label (e.g. antibodies of this invention labeled with a radioisotope, e.g. $^{161}$Tb, $^{123}$I, $^{125}$I and the like), and, after allowing the active substance to be taken up by the target tissue, and preferably after blood clearance of the label, subjecting the mammal to a radioimmunodetection technique in the relevant area of the body, e.g. by using a gamma detecting probe.

In certain embodiments the label-bound antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place. In certain embodiments such methods are particularly useful in localizing and removing secondary cancers produced by metastatic cells from a primary tumor.

In addition to detectable labels, certain preferred effectors include, but are not limited to cytotoxins (e.g. *Pseudomonas* exotoxin, ricin, abrin, *Diphtheria* toxin, and the like), or cytotoxic drugs or prodrugs, in which case the chimeric molecule may act as a potent cell-killing agent specifically targeting the cytotoxin to prostate cancer cells.

In still other embodiments, the effector can include a liposome encapsulating a drug (e.g. an anti-cancer drug such as abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antigen that stimulates recognition of the bound cell by components of the immune system, an antibody that specifically binds immune system components and directs them to the prostate cancer, and the like.

Illustrative Effectors.

Imaging Compositions.

In certain embodiments, the anti-CD46 CPP1 immunoconjugates can be used to direct detectable labels to a tumor site. This can facilitate tumor detection and/or localization. It can be effective for detecting primary tumors, or, in certain embodiments, secondary tumors produced by, e.g., prostate metastatic cells. In certain embodiments, the effector component of the immunoconjugate comprises a "radio-opaque" label, e.g. a label that can be easily visualized using x-rays. Radio-opaque materials are well known to those of skill in the art. The most common radio-opaque materials include iodide, bromide or barium salts. Other radiopaque materials are also known and include, but are not limited to, organic bismuth derivatives (see, e.g., U.S. Pat. No. 5,939,045), radio-opaque polyurethanes (see, e.g., U.S. Pat. No. 5,346,981), organobismuth composites (see, e.g., U.S. Pat. No.

5,256,334), radio-opaque barium polymer complexes (see, e.g., U.S. Pat. No. 4,866,132), and the like.

The anti-CD46 CPP1 antibodies described herein can be coupled directly to the radio-opaque moiety or they can be attached to a "package" (e.g., a chelate, a liposome, a polymer microbead, a nanoparticle, etc.) carrying, containing, or comprising the radio-opaque material, e.g., as described below.

In addition to radio-opaque labels, other labels are also suitable for use. Detectable labels suitable for use in immunoconjugates include any composition detectable by spectroscopic, photochemical, biochemical, immunochemical, electrical, optical or chemical means. Useful labels in the include magnetic beads (e.g., DYNABEADS™), fluorescent dyes (e.g., fluorescein isothiocyanate, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In certain embodiments, suitable radiolabels include, but are not limited to, $^{99}Tc$, $^{203}Pb$, $^{67}Ga$, $^{68}Ga$, $^{72}As$, $^{111}In$, $^{113m}In$, $^{97}Ru$, $^{62}Cu$, $641Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{177}Lu$, $^{105}Rh$, and $^{111}Ag$.

Means of detecting such labels are well known to those of skill in the art. Thus, for example, certain radiolabels may be detected using photographic film, scintillation detectors, PET imaging, MRI, and the like. Fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Radiosensitizers.

In another embodiment, the effector can comprise a radiosensitizer that enhances the cytotoxic effect of ionizing radiation (e.g., such as might be produced by $^{60}Co$ or an x-ray source) on a cell. Numerous radiosensitizing agents are known and include, but are not limited to benzoporphyrin derivative compounds (see, e.g., U.S. Pat. No. 5,945, 439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

Alpha Emitters.

In certain embodiments, the effector can include an alpha emitter, i.e. a radioactive isotope that emits alpha particles. Alpha-emitters have recently been shown to be effective in the treatment of cancer (see, e.g., McDevitt et al. (2001) *Science* 294:1537-1540; Ballangrud et al. (2001) *Cancer Res.* 61: 2008-2014; Borchardt et al. (2003) *Cancer Res.* 63: 5084-50). Suitable alpha emitters include, but are not limited to Bi, $^{213}Bi$, $^{211}At$, and the like.

Chelates

Many of the pharmaceuticals and/or radiolabels described herein can be provided as a chelate. The chelating molecule is typically coupled to a molecule (e.g. biotin, avidin, streptavidin, etc.) that specifically binds an epitope tag attached to an anti-CD46 CPP1 antibody described herein.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N",N"'-tetra-acetic acid (DOTA), hydroxyethyldiamine triacetic acid (HEDTA), 1,4, 8,11-tetra-azacyclotetradecane-N,N',N",N"'-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N,N",N"'-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilonamino group of a lysine residue of the antibody, thereby converting one carboxyl group of DOTA to an amide moiety.

In certain embodiments the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl):154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}IN$ and $^{90}Y$. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

Cytotoxins.

The anti-CD46 CPP1 antibodies described herein can be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters as described above.

Enzymatically active toxins and fragments. thereof are exemplified by *diphtheria* toxin A fragment, nonbinding active fragments of *diphtheria* toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, enomycin, and the tricothecenes, for example. A variety of radionuclides are available for the production of radioconjugated antibodies. Examples include, but are not limited to $^{212}$Bi, $^{131}$I, $^{131}$In, $^{90}$Y, $^{186}$Re, and the like.

In certain embodiments the cytotoxins can include, but are not limited to *Pseudomonas* exotoxins, *Diphtheria* toxins, ricin, abrin and derivatives thereof. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

In certain embodiments the antibody is attached to a preferred molecule in which domain Ia (amino acids 1 through 252) is deleted and amino acids 365 to 380 have been deleted from domain Ib. In certain embodiments all of domain Ib and a portion of domain II (amino acids 350 to 394) can be deleted, particularly if the deleted sequences are replaced with a linking peptide.

In addition, the PE and other cytotoxic proteins can be further modified using site-directed mutagenesis or other techniques known in the art, to alter the molecule for a particular desired application. For example, means to alter the PE molecule in a manner that does not substantially affect the functional advantages provided by the PE molecules described here can also be used and such resulting molecules are intended to be covered herein.

Methods of cloning genes encoding PE fused to various ligands are well known to those of skill in the art (see, e.g., Siegall et al. (1989) *FASEB J.,* 3: 2647-2652; and Chaudhary et al. (1987) *Proc. Natl. Acad. Sci. USA,* 84: 4538-4542).

Like PE, *diphtheria* toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science,* 175: 901-903; Uchida et al. (1973) *J. Biol. Chem.,* 248: 3838-3844).

In certain embodiments, the antibody-*Diphtheria* toxin immunoconjugates of this invention have the native receptor-binding domain removed by truncation of the *Diphtheria* toxin B chain. One illustrative modified *Diphtheria* toxin is DT388, a DT in which the carboxyl terminal sequence beginning at residue 389 is removed (see, e.g., Chaudhary et al. (1991) *Bioch. Biophys. Res. Comm.,* 180: 545-551). Like the PE chimeric cytotoxins, the DT molecules can be chemically conjugated to the prostate cancer specific antibody, but, in certain preferred embodiments, the antibody will be fused to the *Diphtheria* toxin by recombinant means (see, e.g., Williams et al. (1990) *J. Biol. Chem.* 265: 11885-11889).

Viral Particles.

In certain embodiments, the effector comprises a viral particle (e.g., a filamentous phage, an adeno-associated virus (AAV), a lentivirus, and the like). The antibody can be conjugated to the viral particle and/or can be expressed on the surface of the viral particle (e.g. a filamentous phage). The viral particle can additionally include a nucleic acid that is to be delivered to the target (e.g., prostate cancer) cell. The use of viral particles to deliver nucleic acids to cells is described in detail in WO 99/55720, U.S. Pat. No. 6,670,188, U.S. Pat. No. 6,642,051, and U.S. Pat. No. 6,669,936.

Other Therapeutic Moieties.

Figure 9:
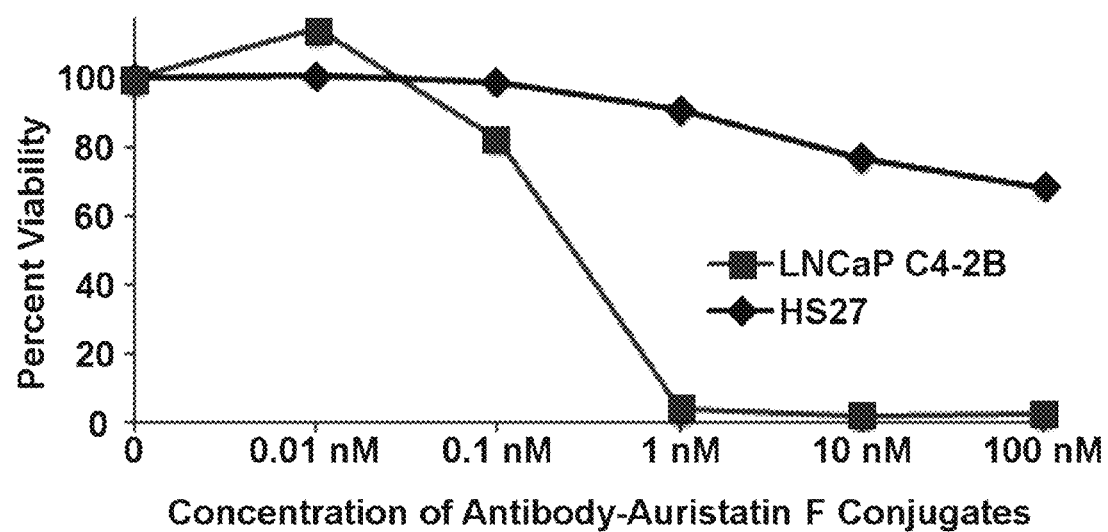
FIG. 9 show that anti-CD46 antibody drug conjugates potently and selectively reduce the viability of a bone-metastasizing prostate cancer cell line. Prostate cancer and control cells were incubated with the 2B10 IgG conjugated to monomethyl auristatin F (2B10-MC-vc-PAB-MMAF) at the indicated concentrations for 96 hrs. Cell viability was assessed by Live/Dead Cell Viability assay (Invitrogen/Life Technologies). IC50 is estimated to be between 200-400 pM. The drug conjugation service was performed by Concortis, Inc. LNCaP C4-2B: a castration resistant bone-metastasizing prostate cancer cell line derived from LNCaP. HS27: a non-tumorigenic human fibroblast cell line that expresses moderate levels of CD46.

Other suitable effector molecules include pharmacological agents or encapsulation systems containing various pharmacological agents. As shown in FIG. 9 anti-CD46 antibody drug conjugates potently and selectively reduce the viability of a bone-metastasizing prostate cancer cell line. Prostate cancer and control cells were incubated with the 2B10 IgG conjugated to monomethyl auristatin F (2B10-MC-vc-PAB-MMAF) at the indicated concentrations for 96 hrs. Cell viability was assessed by Live/Dead Cell Viability assay (Invitrogen/Life Technologies) and IC50 was estimated to be between 200-400 pM.

Thus, in various embodiments, it is recognized that the targeting molecule (e.g., the targeting antibody) can be attached directly or through a linker to a drug that is to be delivered directly to the tumor. Such drugs are well known to those of skill in the art and include, but are not limited to, anti-cancer antibodies (e.g., HERCEPTIN®), antimetabolites, alkylating agents, topoisomerase inhibitors, microtubule targeting agents, kinase inhibitors, protein synthesis inhibitors, somatostatin analogs, glucocorticoids, aromatose inhibitors, mTOR inhibitors, protein Kinase B (PKB) inhibitors, phosphatidylinositol, 3-Kinase (PI3K) Inhibitors, cyclin dependent kinase inhibitors, anti-TRAIL molecules, MEK inhibitors, and the like. In certain embodiments the anti-cancer compounds include, but are not limited to fluorouracil (5-FU), capecitabine/XELODA, 5-Trifluoromethyl-2'-deoxyuridine, methotrexate sodium, raltitrexed/Tomudex, pemetrexed/Alimta®, cytosine Arabinoside (Cytarabine, Ara-C)/Thioguanine, 6-mercaptopurine (Mercaptopurine, 6-MP), azathioprine/Azasan, 6-thioguanine (6-TG)/Purinethol (TEVA), pentostatin/Nipent, fludarabine phosphate/Fludara®, cladribine (2-CdA, 2-chlorodeoxyadenosine)/Leustatin, floxuridine (5-fluoro-2)/FUDR (Hospira, Inc.), ribonucleotide Reductase Inhibitor (RNR), cyclophosphamide/Cytoxan (BMS), neosar, ifosfamide/Mitoxana, thiotepa, BCNU-1,3-bis(2-chloroethyl)-1-nitosourea, 1,-(2-chloroethyl)-3-cyclohexyl-Initrosourea, methyl CCNU, hexamethylmelamine, busulfan/Myleran, procarbazine HCL/Matulane, dacarbazine (DTIC), chlorambucil/Leukaran®, melphalan/Alkeran, cisplatin (Cisplatinum, CDDP)/Platinol, carboplatin/Paraplatin, oxaliplatin/Eloxitan, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin HCL/Doxil, daunorubicin citrate/Daunoxome®, mitoxantrone HCL/Novantrone, actinomycin D, etoposide/Vepesid, topotecan HCL/Hycamtin, teniposide (VM-26), irinotecan HCL(CPT-11)/, Camptosar®, camptothecin, Belotecan, rubitecan, vincristine, vinblastine sulfate, vinorelbine tartrate, vindesine sulphate, paclitaxel/Taxol, docetaxel/Taxotere, nanoparticle paclitaxel, abraxane, ixabepilone, larotaxel, ortataxel, tesetaxel, vinflunine, and the like. In certain embodiments the anti-cancer drug(s) comprise one or more drugs selected from the group consisting of carboplatin (e.g., PARAPLATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antisense molecule, an SiRNA, and the like.

Alternatively, the effector molecule can comprise an encapsulation system, such as a viral capsid, a liposome, or micelle that contains a therapeutic composition such as a drug, a nucleic acid (e.g. an antisense nucleic acid or another nucleic acid to be delivered to the cell), or another therapeutic moiety that is preferably shielded from direct exposure to the circulatory system. Means of preparing liposomes attached to antibodies are well known to those of skill in the art (see, e.g., U.S. Pat. No. 4,957,735, Connor et al. (1985) *Pharm. Ther.,* 28: 341-365, and the like).

B) Attachment of the Antibody to the Effector.

One of skill will appreciate that the anti-CD46 CPP1 antibodies described herein and the effector molecule(s) can be joined together in any order. Thus, where antibody is a single chain polypeptide, the effector molecule can be joined to either the amino or carboxy termini of the targeting molecule. The antibody can also be joined to an internal region of the effector molecule, or conversely, the effector molecule can be joined to an internal location of the antibody, as long as the attachment does not interfere with the respective activities of the molecules.

The antibody and the effector can be attached by any of a number of means well known to those of skill in the art. Typically the effector is conjugated, either directly or through a linker (spacer), to the antibody. However, in certain embodiments, where both the effector molecule is or comprises a polypeptide it is preferable to recombinantly express the chimeric molecule as a single-chain fusion protein.

Conjugation of the Effector Molecule to the Antibody.

In one embodiment, the anti-CD46 CPP1 specific antibody is chemically conjugated to the effector molecule (e.g., a cytotoxin, a label, a ligand, or a drug or liposome, etc.). Means of chemically conjugating molecules are well known to those of skill.

The procedure for attaching an effector to an antibody will vary according to the chemical structure of the effector and/or antibody. Polypeptides typically contain variety of functional groups; e.g., carboxylic acid (COOH) or free amine (—$NH_2$) groups, that are available for reaction with a suitable functional group on an effector molecule to bind the effector thereto.

Alternatively, the antibody and/or the effector can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

The immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

Many procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine,* Academic Press, pp. 168-190 (1982), Waldmann (1991) *Science,* 252: 1657, U.S. Pat. Nos. 4,545,985 and 4,894,443.

In some circumstances, it is desirable to free the effector from the antibody when the immunoconjugate has reached its target site. Therefore, immunoconjugates comprising linkages that are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Conjugation of Chelates.

In certain embodiments, the effector comprises a chelate that is attached to an antibody or to an epitope tag. The anti-CD46 CPP1 specific antibody bears a corresponding epitope tag or antibody so that simple contacting of the antibody to the chelate results in attachment of the antibody with the effector. The combining step can be performed before the moiety is used (targeting strategy) or the target tissue can be bound to the antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

Production of Fusion Proteins.

Where the antibody and/or the effector is relatively short (i.e., less than about 50 amino acids) they can be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

In certain embodiments, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention can be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments DNA encoding fusion proteins of the present invention can be cloned using PCR cloning methods.

While the antibody and the effector are, in certain embodiments, essentially joined directly together, one of skill will appreciate that the molecules can be separated by a spacer, e.g., a peptide spacer consisting of one or more amino acids (e.g., $(Gly_4Ser)_3$, SEQ ID NO:2). Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including E. coli, other bacterial hosts, yeast, and various higher eukaryotic cells such as the COS, CHO and HeLa cells lines and myeloma cell lines. The recombinant protein gene will be operably linked to appropriate expression control sequences for each host.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) Protein Purification, Springer-Verlag, N.Y.; Deutscher (1990) Methods in Enzymology Vol. 182: Guide to Protein Purification., Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Pharmaceutical Compositions.

The anti-CD46 CPP1 antibodies described herein and/or immunoconjugates thereof are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the antibodies described herein and/or immunoconjugates thereof and pharmaceutical compositions comprising antibodies described herein and/or immunoconjugates thereof, when administered orally, are preferably protected from digestion. This can be accomplished by a number of means known to those of skill in the art, e.g., by complexing the protein with a composition to render it resistant to acidic and enzymatic hydrolysis or by packaging the protein in an appropriately resistant carrier such as a liposome. Means of protecting proteins from digestion are well known in the art.

In various embodiments a composition, e.g., a pharmaceutical composition, containing one or a combination of anti-CD46 CPP1 antibodies, or antigen-binding portion(s) thereof, or immunoconjugates thereof, formulated together with a pharmaceutically acceptable carrier are provided.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, may be coated in a material to protect the compound from the action of acids and other natural conditions that may inactivate the compound.

In certain embodiments the antibody and/or immunoconjugate can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience, and as described above.

By way of illustration, a pharmaceutically acceptable salt can be prepared for any of the antibodies and/or immunoconjugates described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the antibody and/or immunoconjugate. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

Pharmaceutical compositions comprising the antibodies and/or immunoconjugates described herein can be administered alone or in combination therapy, i.e., combined with other agents. For example, the combination therapy can include a an antibody or immunoconjugate with at least one or more additional therapeutic agents, such as the anti-cancer agents described infra. The pharmaceutical compositions can also be administered in conjunction with radiation therapy and/or surgery.

A composition comprising the antibodies and/or immunoconjugates described herein can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson, ed., Marcel Dekker, Inc., New York, 1978).

In certain embodiments administration of an anti-CD46 CPP1 antibody or immunoconjugate may be facilitated by coating the antibody or immunoconjugate composition, or co-administering the antibody or immunoconjugate, a material to prevent its inactivation. For example, the compound may be administered to a subject in an appropriate carrier, for example, liposomes, or a diluent. Pharmaceutically acceptable diluents include, but are not limited to, saline and aqueous buffer solutions. Liposomes include, but are not limited to, water-in-oil-in-water CGF emulsions as well as conventional liposomes (Strejan et al. (1984) *J. Neuroimmunol*, 7: 27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of is contemplated. Supplementary active compounds can also be incorporated into the compositions.

In various embodiments the therapeutic compositions are typically sterile and stable under the conditions of manufacture and storage. The composition(s) can be formulated as a solution, a microemulsion, in a lipid or liposome, or other ordered structure suitable to contain high drug concentration(s). In certain embodiments the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound (e.g., antibodies and/or immunoconjugates described herein) in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, illustrative methods of preparation include vacuum drying, and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, in certain embodiments, the antibodies and/or immunoconjugates described herein may be administered once or twice daily, or once or twice weekly, or once or twice monthly by subcutaneous injection.

It is especially advantageous to formulate parenteral compositions in unit dosage form for ease of administration and uniformity of dosage. Unit dosage form as used herein refers to physically discrete units suited as unitary dosages for the subjects to be treated. Each unit contains a predetermined quantity of active compound calculated to produce the desired therapeutic effect in association with the required pharmaceutical carrier. The specifications for the unit dosage forms are dictated by and directly dependent on (a) the unique characteristics of the active compound and the particular therapeutic effect to be achieved, and (b) the limitations inherent in the art of compounding such an active compound for the treatment of individuals.

In certain embodiments the formulation comprises a pharmaceutically anti-oxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like;

(2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the antibodies and/or immunoconjugates described herein include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient that can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of antibodies and/or immunoconjugates described herein that are suitable for vaginal administration also include pessaries, tampons, creams, gels, pastes, foams or spray formulations containing such carriers as are known in the art to be appropriate. Dosage forms for the topical or transdermal administration of antibodies and/or immunoconjugates described herein include powders, sprays, ointments, pastes, creams, lotions, gels, solutions, patches and inhalants. In certain embodiments the active compound may be mixed under sterile conditions with a pharmaceutically acceptable carrier, and with any preservatives, buffers, or propellants that may be required.

The phrases "parenteral administration" and "administered parenterally" as used herein means modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion.

Examples of suitable aqueous and nonaqueous carriers that may be employed in the pharmaceutical compositions comprising antibodies and/or immunoconjugates described herein include, but are not limited to water, ethanol, polyols (such as glycerol, propylene glycol, polyethylene glycol, and the like), and suitable mixtures thereof, vegetable oils, such as olive oil, and injectable organic esters, such as ethyl oleate, and the like. Proper fluidity can be maintained, for example, by the use of coating materials, such as lecithin, by the maintenance of the required particle size in the case of dispersions, and by the use of surfactants.

In various embodiments these compositions may also contain adjuvants such as preservatives, wetting agents, emulsifying agents and dispersing agents. Particular examples of adjuvants that are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes that contain a membrane-bound hemagglutinin and neuraminidase derived from the influenza virus).

Prevention of presence of microorganisms in formulations may be ensured both by sterilization procedures, and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When the antibodies and/or immunoconjugates described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the antibodies and/or immunoconjugates described herein, that may be used in a suitable hydrated form, and/or the pharmaceutical compositions, are formulated into pharmaceutically acceptable dosage forms by conventional methods known to those of skill in the art.

Actual dosage levels of the active ingredients (e.g., antibodies and/or immunoconjugates described herein) in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of antibodies and/or immunoconjugates described herein will be that amount of the compound which is the lowest dose effective to produce a therapeutic effect. Such an effective dose will generally depend upon the factors described above. In certain embodiments, it is preferred that administration be intravenous, intramuscular, intraperitoneal, or subcutaneous, preferably administered proximal to the site of the target. If desired, the effective daily dose of a therapeutic composition may be administered a single dosage, or as two, three, four, five, six or more sub-doses administered separately at appropriate intervals throughout the day, optionally, in unit dosage forms. While it is possible for antibodies and/or immunoconjugates described herein to be administered alone, it is typically preferable to administer the compound(s) as a pharmaceutical formulation (composition).

In certain embodiments the therapeutic compositions can be administered with medical devices known in the art. For example, in a illustrative embodiment, antibodies and/or immunoconjugates described herein can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of useful well-known implants and modules are described for example in U.S. Pat. No. 4,487,603, which discloses an implantable micro-infusion pump for dispensing medication at a controlled rate, in U.S. Pat. No. 4,486,194, which discloses a therapeutic device for administering medications through the skin, in U.S. Pat. No. 4,447,233, which discloses a medication infusion pump for delivering medication at a precise infusion rate, in U.S. Pat. No. 4,447,224, which discloses a variable flow implantable infusion apparatus for continuous drug delivery, in U.S. Pat. No. 4,439,196, which discloses an osmotic drug delivery system having multi-chamber compartments, and in U.S. Pat. No. 4,475,196, which discloses an osmotic drug delivery system. Many other such implants, delivery systems, and modules are known to those skilled in the art.

In certain embodiments, the anti-CD46 CPP1 antibodies and/or immunoconjugates described herein can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade (1989) *J. Clin. Pharmacol.* 29: 685). Illustrative targeting moieties include, but are not limited to folate or biotin (see, e.g., U.S. Pat. No. 5,416,016); mannosides (Umezawa et al., (1988) *Biochem. Biophys. Res. Commun.* 153: 1038); antibodies (Bloeman et al. (1995) *FEBS Lett.* 357:140; Owais et al. (1995) *Antimicrob. Agents Chemother.* 39:180); surfactant protein A receptor (Briscoe et al. (1995) *Am. J. Physiol.* 1233:134).

Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

In certain embodiments, such a kit comprises one or more antibodies or immumoconjugates described herein. The antibodies or immumoconjugates can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the immunoconjugate can simply be produced by combining the components in a neutral medium and causing them to react. For that purpose the effector may be presented to the antibody, for example, in the form of a chelate.

When kit constituent(s) are used as component(s) for pharmaceutical administration (e.g. as an injection liquid) they are preferably sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Human Monoclonal Antibody that Induces Tumor-Selective Internalization of CD46 and Epitope Therein We have previously identified a prostate tumor targeting internalizing human monoclonal antibody that binds to prostate tumor cells in situ residing in their tissue microenvironment. We hereby identified the antigen bound by this antibody as human CD46 by immunoprecipitation and mass spectrometry analysis. We further mapped the binding epitope. We determined that the epitope is conformational and located in the Sushi domain 1 of CD46. Furthermore, a 15 amino acid region in Sushi 1 is necessary for binding. Interestingly, we found that our anti-CD46 antibody binding to this epitope is preferentially internalized by prostate tumor cells with no significant internalization by normal cells that express CD46. Furthermore, we performed functional internalization studies using antibody-toxin (saporin) conjugates. We found that our anti-CD46 antibody-toxin conjugate preferentially kills prostate cancer cells, consistent with the differential internalization that we have observed for tumor cells. To further determine if this CD46 epitope is an excellent therapeutic target, we performed immunohistochemistry studies using a panel of normal and prostate tumor tissues. We found that this CD46 epitope is expressed by all prostate tumors that we have studied but is not expressed in any significant way by a broad panel of normal human tissues except the placental trophoblasts, which are not present in men, and the normal prostate, which is not a vital organ. Thus this CD46 epitope that we have identified can be targeted by our human monoclonal antibody to allow tumor-selective internalization and targeted tumor killing by antibody-toxin or antibody-drug conjugates.

Results

Identification of the Target Antigen as Human CD46

We have previously identified a human single chain antibody UA20 that (1) is internalizing, (2) binds to prostate tumor cells in situ, (3) binds to prostate cancer cell line DU145, PC3 and LnCaP but not to control cells such as benign prostatic hyperplasia epithelial cell line BPH-1. In order to identify the cell surface antigen bound by UA20, we performed immunoprecipitation (IP) studies using cell lysates prepared from surface biotin-labeled prostate cancer cell line DU145. The biotin-labeling agent (EZ-Link Sulfo-NHS-Biotin, Pierce) is non-membrane permeable and thus preferentially labels cell surface proteins. UA20 scFv were covalently linked to protein A beads using the chemical crosslinker DSP (Pierce). As shown in FIG. 1, panels A and B, two bands of biotinylated proteins of 55 kDa and 72 kDa were pulled down by the UA20 ScFv immobilized to protein A beads. Mass spectrometry analysis identified both bands as human CD46. Human CD46 is a highly glycosylated protein that migrates as two bands on sodium dodecyl sulfate polyacrylamide gel electrophoresis (SDS-PAGE) with apparent molecular weights between 55-72 kDa. To confirm the antigen identification result, we repeat the IP with UA20 scFv using cell lysates prepared from surface biotin-labeled prostate cancer cell line DU145 and the control cell line BPH, and analyzed the IP products by Western Blot with a murine monoclonal antibody (mAb) against human CD46 and as a reference streptavidin-HRP. As shown in FIG. 1, panel C, both streptavidin-HRP and anti-CD46 mAb recognize the same two bands from the Du145 IP product but not the BPH-1 IP product, confirming that UA20 binds to CD46. To further verify the identification results, we cloned human CD46 and expressed it in 293 cells via transient transfection. As shown in FIG. 1, panel D, binding of UA20 to CD46-transfected 293 cells is significantly increased compared to control cDNA-transfected 293 cells.

UA20 Binds to CCP-1, a Non-Complement Regulatory Domain of CD46

CD46 is a transmembrane glycoprotein that is also known as membrane cofactor protein (MCP). The extracellular portion of CD46 consists of four modules known as complement control protein repeats (CCPs) or sushi domains. The four CCPs is followed by a serine, threonine, proline-rich (STP) region that is highly glycosylated (O-linked). CCP2, CCP3 and CCP4 are important for ligand binding and complement regulatory function, whereas the CCP1 and CCP2 domains are critical for measles virus binding.

Figure 2:
FIG. 2 illustrates deletion mapping to identify UA20 binding site. CCP deletions were constructed as indicated, transfected into 293T cells and tested by FACS for binding to UA20. "−" indicates no significant binding. "+++" and "++++" indicates strong binding. "++" indicated reduced binding compared to wild type CD46-transfected cells. ECD: extracellular domain. TM: transmembrane. ICD: intracellular domain.

To identify the UA20 binding epitope on CD46, we made the following deletion mutants: CCP1 deletion mutant (CCPde1), CCP1 and CCP 2 double-deletion mutant (CCPde(1, 2)), CCP2 deletion mutant (CCPde2), CCP3 deletion mutant (CCPde3) and CCP4 deletion mutant (CCPde4). We tested binding by FACS of UA20 binding to 293 cells transfected with these mutant plasmids. As shown in FIG. 2, UA20 binds to 293 cells transfected with full-length human CD46, deletion mutants CCPde2 and CCPde3, but not CCPde11 and CCPde(1, 2). Binding to CCPde4 is partially affected. These results suggest that the UA20 epitope is a conformational epitope with the primary binding site residing in CCP1.

Figure 3:
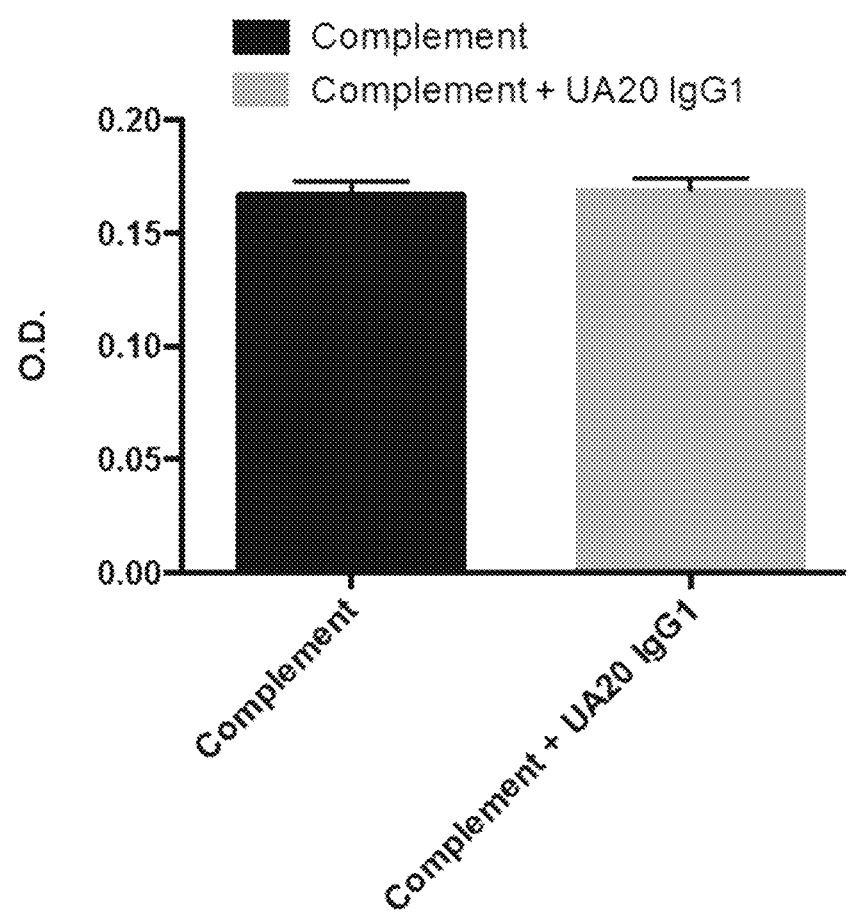
FIG. 3 shows that UA20 IgG1 does not interfere with the complement regulation function of CD46. Human PBMC cells were incubated with human complement enriched serum at 37° C. for 4 h and cell viability was measured by CCK-8 cell counting kit. The experiment was done in triplicates and no significant difference was observed (t-test).

UA20 does not Affect Normal Complement Regulation:

Because CCP1 is not involved in complement regulatory function of CD46, binding of UA20 to this domain is not expected to induce complement dependent cytotoxicity (CDC). As shown in FIG. 3, UA20 IgG1 did not trigger CDC in the cells that we have studied including human peripheral blood mononuclear cells (PBMCs).

Internalization Via a Macropinocytosis-Like Pathway:

We found that UA20 IgG is internalized by tumor cells via a macropinocytosis-like pathway. Using laser confocal microscopy, we found that UA20 IgG co-localized with the classic macropinocytosis marker dextran (ND70) (FIG. 4). Interestingly, macropinocytosis has been shown to be a tumor-selective internalization pathway. This selective internalization mechanism is highly exploitable for therapeutic development based on CD46 targeting.

Figure 5:
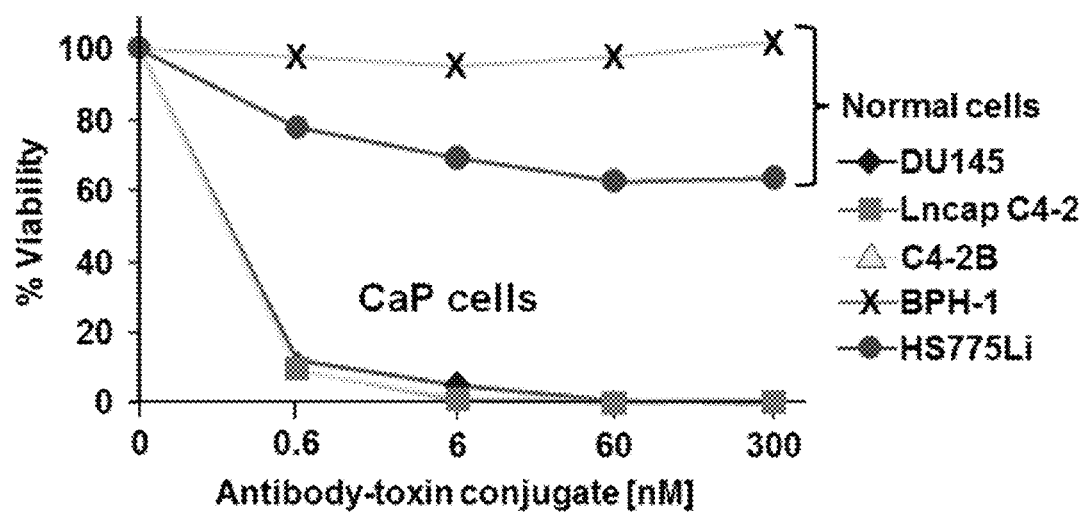
FIG. 5 illustrates elective killing of prostate cancer cells by UA20-toxin conjugates. Biotin-labeled UA20 IgG1 was incubated with streptavidin-saporin to form the antibody-toxin conjugate, which was incubated with a panel of prostate cancer and control cells at varying concentrations at 37° C. for 72-96 h. Cell viability was determined using the CCK-8 cell counting kit. Prostate cancer (CaP) cells: Du145, LNCaP $C_{4-2}$ (a castration resistant subline) and $C_{4-2}B$ (a bone metastasizing castration resistant subline). HS775Li: A primary non-tumorigenic human liver cell line. BPH-1: a cell line derived from non-tumorigenic benign prostatic hyperplasia.

Selective Killing of Tumor Cells by Anti-CD46 Antibody-Toxin Conjugates:

The afore-described selective internalization prompted us to test if tumor cells can be selectively killed by toxin-conjugated antibody binding to the CD46 epitope that we have defined. We biotin-labeled UA20 IgG1 and mixed with streptavidin-labeled saporin toxin to form the antibody-toxin conjugate. Saporin is found in seeds and leaves of the plant *Saponaria officinalis* and belongs to class I ribosome-inactivating proteins. Saporin by itself cannot enter living cells and is not toxic, but becomes potently cytotoxic when translocated to the cytosol via a carrier that is capable of entering living cells. Antibody-saporin conjugate is toxic to the target cell only when the antibody is internalizing. We performed this functional internalization assay and found that the UA20-saporin conjugate preferentially kills prostate cancer cells (FIG. 5), leaving normal cells little affected even if they express modest levels of CD46 (see HS775LI in FIG. 5).

Figure 6:
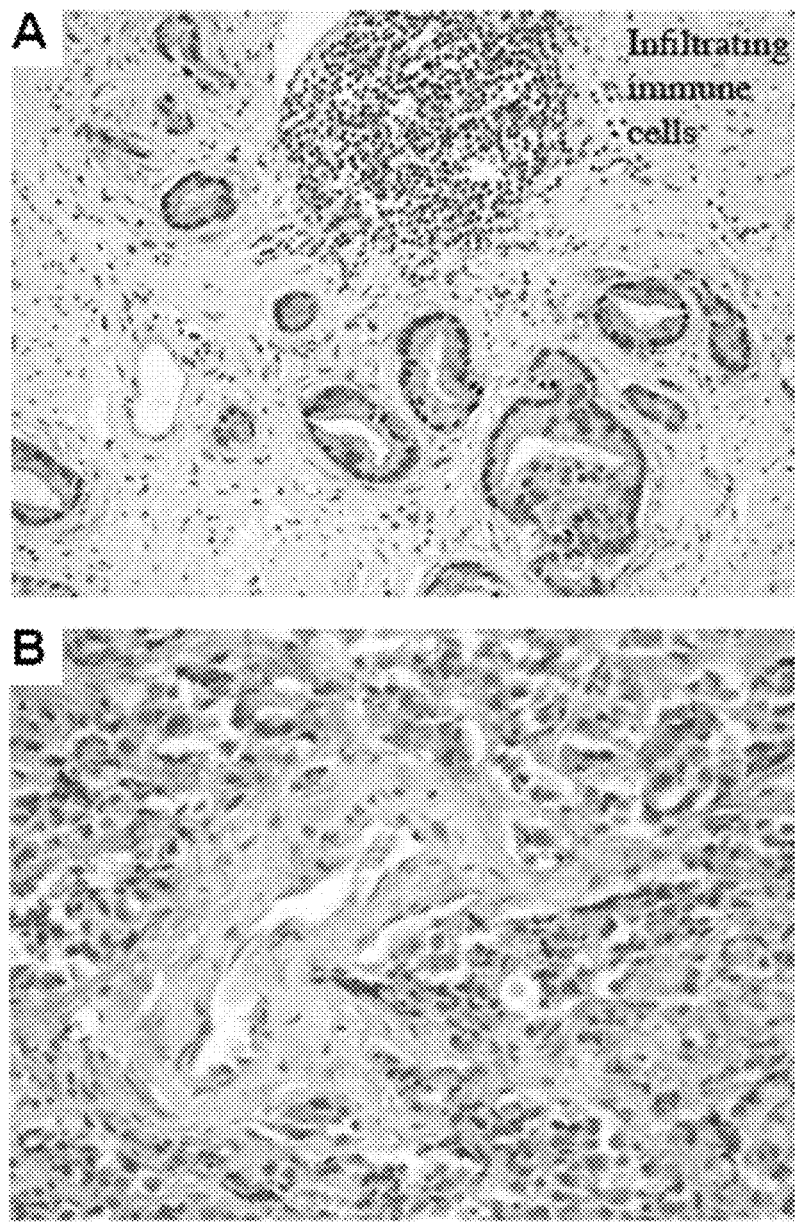
FIG. 6, panels A and B, illustrate the results of an immunohistochemistry (IHC) study of CD46 expression in prostate cancer tissues. Expressions were detected in both primary tumor (panel A, n=18, all positive) and bone mets (panel B, n=3, all positive). Representative images are shown. Note that infiltrating immune cells are not stained compared to tumor cells, indicating a large differential in the amount of CD46 expressed by tumor vs normal cells.

CD46 Epitope Expression in Tumor and Normal Human Tissues:

We performed immunohistochemistry to study tissue distribution of CD46. UA20 stained 18/18 frozen prostate cancer tissues (FIG. 6). To study expression on normal tissues, we used the FDA standard normal frozen tissue panel for therapeutic antibody evaluation (US Biomax) that contains 90 tissues cores (30 organ sites from 3 individuals). We found that most of the normal human tissues expressed very low levels of the UA20 epitope except the placental trophoblasts and prostate glands. Because the normal prostate is not a vital organ and placenta trophoblasts are not present in men, the CD46 epitope is an excellent target for developing antibody-based targeted therapy as it mediates tumor-preferred internalization as afore-described.

Identification of a New Anti-CD46 Human Antibody 2B10:

We have re-screened the laser capture microdissection (LCM)-selected prostate tumor binding antibodies by transferring the scFv genes from phage to yeast to create a yeast surface displayed human scFv library that is enriched for cell surface binding antibodies. Following two rounds of selection on live prostate tumor cells, we identified a new anti-CD46 antibody 2B10. While UA20 and 2B10 share homologies, they have a different heavy chain CDR1 sequence (FIG. 8). Nonetheless, 2B10 also bind to human CD46 and compete with UA20, indicating that they bind to the same or closely related epitope.

Figure 7A:
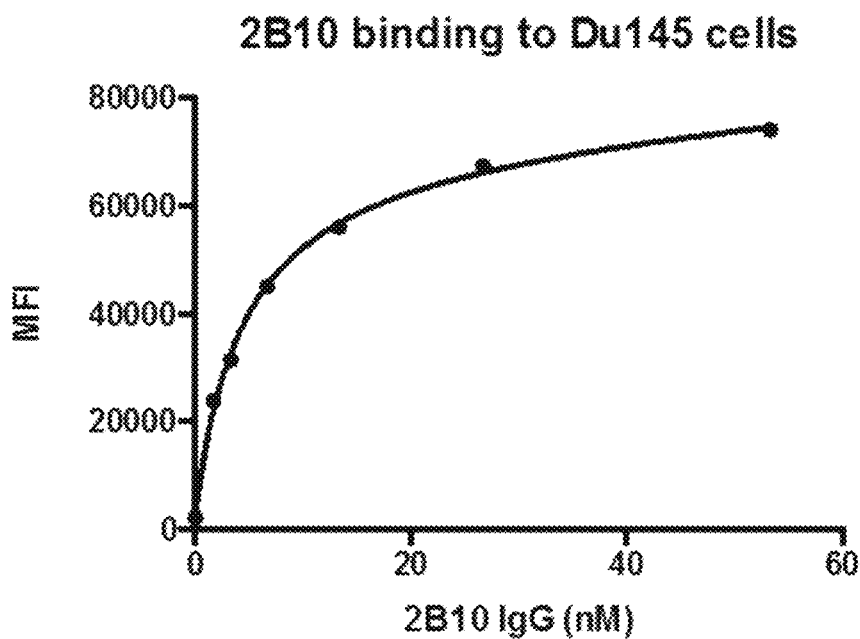
FIGS. 7A and 7B show apparent binding affinity measured on live tumor cells for 2B10 (FIG. 7A) and for UA20 (FIG. 7B). Antibodies were incubated with Du145 cells at 4° C., washed and binding detected by FACS using PE-conjugated anti-human Fc secondary antibodies. GraphPad was used to fit the binding curve. In the particular experiment set shown below, KD for 2B10 is 4.5 nM, while UA20 10.6 nM. Generally speaking, when measured side-by-side, 2B10 consistently shows a higher affinity than UA20 (1-5 nM vs 5-10 nM).
Figure 7B:
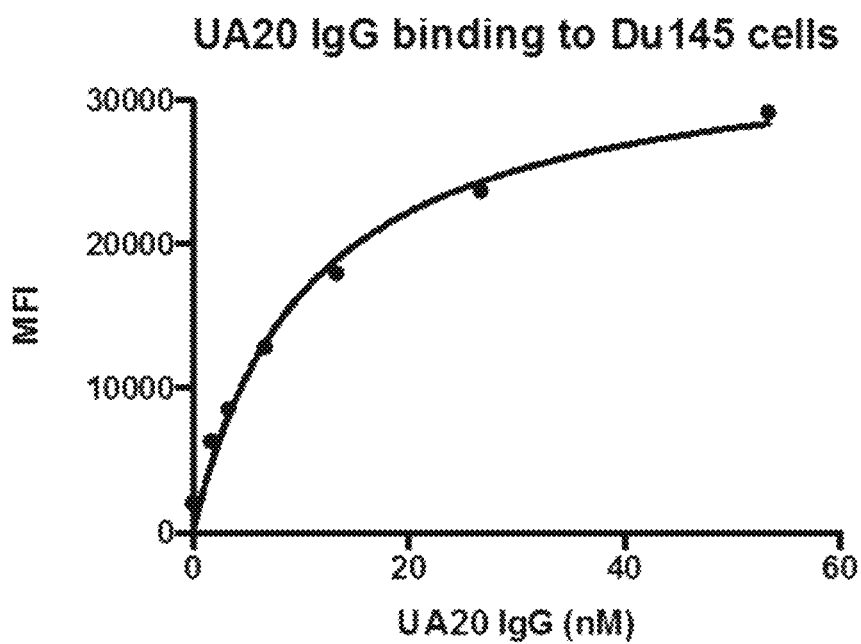

We converted both UA20 and 2B10 into human IgG1s. We found that 2B10 IgG1 has higher affinity towards prostate cancer cells. Measured on live tumor cells by FACS, the apparent KD for 2B10 is about 1-5 nM while for UA20 about 5-10 nM (FIG. 7).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antibody that specifically binds and is internalized into a prostate cancer cell, wherein:
   said antibody is an antibody that specifically binds cells that express or overexpress a CD46, wherein said antibody specifically binds sushi domain 1 of said CD46; and
   said antibody comprises VH CDR1, VH CDR2, and VH CDR3 of the 2B10 antibody and VL CDR1, VL CDR2, and VL CDR3 of the 2B10 antibody.

2. The antibody of claim 1, wherein said cells that express or overexpress a CD46 are prostate cancer cells.

3. The antibody of claim 1, wherein said antibody bind cells of a cell line selected from the group consisting of DU145 cells, PC3 cells, and LnCaP cells.

4. The antibody of claim 1, wherein said antibody is a substantially intact immunoglobulin.

5. The antibody of claim 4, wherein said antibody comprises an IgA, IgE, or IgG isotype.

6. The antibody of claim 1, wherein said antibody is an antibody fragment selected from the group consisting of Fv, Fab, (Fab')$_2$, (Fab')$_3$, IgGΔCH2, and a minibody.

7. The antibody of claim 1, wherein said antibody is a single chain antibody.

8. The antibody of claim 7, wherein the VL region of said antibody is attached to the VH region of said antibody by an amino acid linker ranging in length from about 3 amino acids up to about 15 amino acids.

9. The antibody of claim 7, wherein the VL region of said antibody is attached to the VH region of said antibody by an amino acid linker selected from the group consisting of GGGGS GGGGS GGGGS (SEQ ID NO:2), GGGGS GGGGS (SEQ ID NO:3), GGGGS (SEQ ID NO:4), GS GGGGS GGGGS GGS GGGGS (SEQ ID NO:5), SGGGGS (SEQ ID NO:6), GGGS (SEQ ID NO:7), VPGV (SEQ ID NO:8), VPGVG (SEQ ID NO:9), GVPGVG (SEQ ID NO:10), GVG VP GVG (SEQ ID NO:11), VP GVG VP GVG (SEQ ID NO:12), GGSSRSS (SEQ ID NO:13), and GGSSRSSSSGGGGSGGGG (SEQ ID NO:14).

10. The antibody of claim 1, wherein said antibody comprises the variable light (VL) chain of the 2B10 antibody and the variable heavy (VH) chain of the 2B10 antibody.

11. The antibody of claim 1, wherein said antibody is a human scFv.

12. The antibody of claim 1, wherein said antibody is a human 2B10 IgG.

13. An immunoconjugate comprising an antibody of claim 1 attached to an effector wherein said effector is selected from the group consisting of a second antibody, a detectable label, a cytotoxin or cytostatic agent, a liposome containing a drug, a radionuclide, a drug, a prodrug, a viral particle, a cytokine, and a chelate.

14. A pharmaceutical formulation said formulation comprising:
   a pharmaceutically acceptable excipient and an antibody of claim 1 or a pharmaceutically acceptable excipient and a immunoconjugate of claim 13.

15. The immunoconjugate of claim 13, wherein said antibody comprises the variable light (VL) chain of the 2B10 antibody and the variable heavy (VH) chain of the 2B10 antibody.

16. The immunoconjugate of claim 13, wherein said antibody is a substantially intact immunoglobulin.

17. The immunoconjugate of claim 15, wherein said antibody is a substantially intact immunoglobulin.

18. The immunoconjugate of claim 13, wherein said antibody is a single chain antibody.

19. The immunoconjugate of claim 13, wherein said antibody is the 2B10 antibody.

20. The immunoconjugate of claim 13, wherein said effector is an anticancer drug.

21. The antibody of claim 1, wherein said antibody is the 2B10 antibody.

22. The antibody of claim 10, wherein said antibody is a substantially intact immunoglobulin.

23. The antibody of claim 22, wherein said antibody comprises an IgA, IgE, or IgG isotype.

24. The antibody of claim 10, wherein said antibody is an antibody fragment selected from the group consisting of Fv, Fab, (Fab')$_2$, (Fab')$_3$, IgGΔCH2, and a minibody.

25. The antibody of claim 10, wherein said antibody is a single chain antibody.

26. The antibody of claim 25, wherein the VL region of said antibody is attached to the VH region of said antibody by an amino acid linker ranging in length from about 3 amino acids up to about 15 amino acids.

27. The antibody of claim 26, wherein the VL region of said antibody is attached to the VH region of said antibody by an amino acid linker selected from the group consisting of GGGGS GGGGS GGGGS (SEQ ID NO:2), GGGGS GGGGS (SEQ ID NO:3), GGGGS (SEQ ID NO:4), GS GGGGS GGGGS GGS GGGGS (SEQ ID NO:5), SGGGGS (SEQ ID NO:6), GGGS (SEQ ID NO:7), VPGV (SEQ ID NO:8), VPGVG (SEQ ID NO:9), GVPGVG (SEQ ID NO:10), GVG VP GVG (SEQ ID NO:11), VP GVG VP GVG (SEQ ID NO:12), GGSSRSS (SEQ ID NO:13), and GGSSRSSSSGGGGSGGGG (SEQ ID NO:14).

28. A pharmaceutical formulation comprising:
   an antibody comprising the variable light (VL) chain of the 2B10 antibody and the variable heavy (VH) chain of the 2B10 antibody; and
   a pharmaceutically acceptable excipient.

29. A pharmaceutical formulation said formulation comprising:
   2B10 antibody; and
   a pharmaceutically acceptable excipient.

30. A pharmaceutical formulation said formulation comprising:
   an immunoconjugate comprising the 2B10 antibody attached to an effector wherein said effector is selected from the group consisting of a second antibody, a detectable label, a cytotoxin or cytostatic agent, a liposome containing a drug, a radionuclide, a drug, a prodrug, a viral particle, a cytokine, and a chelate; and
   a pharmaceutically acceptable excipient.

* * * * *